(12) United States Patent
Scirica et al.

(10) Patent No.: US 9,987,008 B2
(45) Date of Patent: *Jun. 5, 2018

(54) APPARATUS FOR ENDOSCOPIC PROCEDURES

(71) Applicant: Covidien LP, Mansfield, MA (US)

(72) Inventors: Paul Scirica, Huntington, CT (US); Justin Williams, Southbury, CT (US)

(73) Assignee: Covidien LP, Mansfield, MA (US)

( * ) Notice: Subject to any disclaimer, the term of this patent is extended or adjusted under 35 U.S.C. 154(b) by 314 days.

This patent is subject to a terminal disclaimer.

(21) Appl. No.: 14/970,991

(22) Filed: Dec. 16, 2015

(65) Prior Publication Data

US 2016/0095596 A1 Apr. 7, 2016

Related U.S. Application Data

(63) Continuation of application No. 13/769,414, filed on Feb. 18, 2013, now Pat. No. 9,216,013.

(51) Int. Cl.
*A61B 17/00* (2006.01)
*A61B 17/072* (2006.01)
(Continued)

(52) U.S. Cl.
CPC .. *A61B 17/07207* (2013.01); *A61B 17/00234* (2013.01); *F16H 25/20* (2013.01);
(Continued)

(58) Field of Classification Search
CPC .. A61B 2017/00473; A61B 2017/0046; A61B 2017/2943; A61B 2017/00398;
(Continued)

(56) References Cited

U.S. PATENT DOCUMENTS 2,777,340 A 1/1957 Hettwer et al.
2,957,353 A 10/1960 Babacz
(Continued)

FOREIGN PATENT DOCUMENTS

AU 2008229795 A1 4/2009
CA 2451558 A1 1/2003
(Continued)

OTHER PUBLICATIONS

Extended European Search Report corresponding to International Application No. EP 15 15 1076.5 dated Apr. 22, 2015.
(Continued)

*Primary Examiner* — Gregory Anderson

(57) ABSTRACT

A shaft assembly is provided for interconnecting at least one rotatable drive shaft of a hand-held electromechanical surgical device, and an end effector actuatable by an axial drive force. The shaft assembly includes a flexible drive cable rotatably supported in an outer tube, the flexible drive cable includes a proximal end operatively connected to a respective rotatable drive shaft of the hand-held surgical device. The flexible drive cable being off set a radial distance from a central longitudinal axis of the outer tube. The shaft assembly includes an articulation rod at least partially slidably supported in the outer tube, and an articulation link having a proximal end pivotally connected to the distal end of the articulation rod and a distal end pivotally connected to a distal neck housing. The articulation rod being off set a radial distance from the central longitudinal axis of the outer tube.

18 Claims, 15 Drawing Sheets

(51) Int. Cl.
*F16H 25/20* (2006.01)
*A61B 17/29* (2006.01)

(52) U.S. Cl.
CPC .......... *A61B 2017/0046* (2013.01); *A61B 2017/00398* (2013.01); *A61B 2017/00473* (2013.01); *A61B 2017/00734* (2013.01); *A61B 2017/2903* (2013.01); *A61B 2017/2927* (2013.01); *A61B 2017/2929* (2013.01); *A61B 2017/2943* (2013.01)

(58) Field of Classification Search
CPC ...... A61B 2017/2927; A61B 17/07207; A61B 17/00234
See application file for complete search history.

(56) References Cited

U.S. PATENT DOCUMENTS

| | | | |
|---|---|---|---|
| 3,111,328 A | 11/1963 | Di Rito et al. | |
| 3,695,058 A | 10/1972 | Keith, Jr. | |
| 3,734,515 A | 5/1973 | Dudek | |
| 3,759,336 A | 9/1973 | Marcovitz et al. | |
| 4,162,399 A | 7/1979 | Hudson | |
| 4,606,343 A | 8/1986 | Conta et al. | |
| 4,705,038 A | 11/1987 | Sjostrom et al. | |
| 4,722,685 A | 2/1988 | de Estrada et al. | |
| 4,823,807 A | 4/1989 | Russell et al. | |
| 4,874,181 A | 10/1989 | Hsu | |
| 5,129,118 A | 7/1992 | Walmesley | |
| 5,129,570 A | 7/1992 | Schulze et al. | |
| 5,152,744 A | 10/1992 | Krause et al. | |
| 5,301,061 A | 4/1994 | Nakada et al. | |
| 5,312,023 A | 5/1994 | Green et al. | |
| 5,326,013 A | 7/1994 | Green et al. | |
| 5,350,355 A | 9/1994 | Sklar | |
| 5,383,874 A | 1/1995 | Jackson et al. | |
| 5,383,880 A | 1/1995 | Hooven | |
| 5,389,098 A | 2/1995 | Tsuruta et al. | |
| 5,395,033 A | 3/1995 | Byrne et al. | |
| 5,400,267 A | 3/1995 | Denen et al. | |
| 5,405,073 A | 4/1995 | Porter | |
| 5,411,508 A | 5/1995 | Bessler et al. | |
| 5,413,267 A | 5/1995 | Solyntjes et al. | |
| 5,427,087 A | 6/1995 | Ito et al. | |
| 5,433,721 A | 7/1995 | Hooven et al. | |
| 5,467,911 A | 11/1995 | Tsuruta et al. | |
| 5,476,379 A | 12/1995 | Disel | |
| 5,487,499 A | 1/1996 | Sorrentino et al. | |
| 5,518,163 A | 5/1996 | Hooven | |
| 5,518,164 A | 5/1996 | Hooven | |
| 5,526,822 A | 6/1996 | Burbank et al. | |
| 5,529,235 A | 6/1996 | Boiarski et al. | |
| 5,535,934 A | 7/1996 | Boiarski et al. | |
| 5,535,937 A | 7/1996 | Boiarski et al. | |
| 5,540,375 A | 7/1996 | Bolanos et al. | |
| 5,540,706 A | 7/1996 | Aust et al. | |
| 5,542,594 A | 8/1996 | McKean et al. | |
| 5,549,637 A | 8/1996 | Crainich | |
| 5,553,675 A | 9/1996 | Pitzen et al. | |
| 5,562,239 A | 10/1996 | Boiarski et al. | |
| 5,564,615 A | 10/1996 | Bishop et al. | |
| 5,609,560 A | 3/1997 | Ichikawa et al. | |
| 5,626,587 A | 5/1997 | Bishop et al. | |
| 5,632,432 A | 5/1997 | Schulze et al. | |
| 5,645,209 A | 7/1997 | Green et al. | |
| 5,647,526 A | 7/1997 | Green et al. | |
| 5,653,374 A | 8/1997 | Young et al. | |
| 5,658,300 A | 8/1997 | Bito et al. | |
| 5,662,662 A | 9/1997 | Bishop et al. | |
| 5,667,517 A | 9/1997 | Hooven | |
| 5,693,042 A | 12/1997 | Boiarski et al. | |
| 5,704,534 A | 1/1998 | Huitema et al. | |
| 5,713,505 A | 2/1998 | Huitema | |
| 5,762,603 A | 6/1998 | Thompson | |
| 5,779,130 A | 7/1998 | Alesi et al. | |
| 5,782,396 A | 7/1998 | Mastri et al. | |
| 5,782,397 A | 7/1998 | Koukline | |
| 5,792,573 A | 8/1998 | Pitzen et al. | |
| 5,797,536 A | 8/1998 | Smith et al. | |
| 5,820,009 A | 10/1998 | Melling et al. | |
| 5,863,159 A | 1/1999 | Lasko | |
| 5,865,361 A | 2/1999 | Milliman et al. | |
| 5,908,427 A | 6/1999 | McKean et al. | |
| 5,954,259 A | 9/1999 | Viola et al. | |
| 5,964,774 A | 10/1999 | McKean et al. | |
| 5,993,454 A | 11/1999 | Longo | |
| 6,010,054 A | 1/2000 | Johnson et al. | |
| 6,017,354 A | 1/2000 | Culp et al. | |
| 6,032,849 A | 3/2000 | Mastri et al. | |
| 6,045,560 A | 4/2000 | McKean et al. | |
| 6,090,123 A | 7/2000 | Culp et al. | |
| 6,126,651 A | 10/2000 | Mayer | |
| 6,129,547 A | 10/2000 | Cise et al. | |
| 6,165,169 A | 12/2000 | Panescu et al. | |
| 6,239,732 B1 | 5/2001 | Cusey | |
| 6,241,139 B1 | 6/2001 | Milliman et al. | |
| 6,264,086 B1 | 7/2001 | McGuckin, Jr. | |
| 6,264,087 B1 | 7/2001 | Whitman | |
| 6,302,311 B1 | 10/2001 | Adams et al. | |
| 6,315,184 B1 | 11/2001 | Whitman | |
| 6,321,855 B1 | 11/2001 | Barnes | |
| 6,329,778 B1 | 12/2001 | Culp et al. | |
| 6,343,731 B1 | 2/2002 | Adams et al. | |
| 6,348,061 B1 | 2/2002 | Whitman | |
| 6,368,324 B1 | 4/2002 | Dinger et al. | |
| 6,371,909 B1 | 4/2002 | Hoeg et al. | |
| 6,434,507 B1 | 8/2002 | Clayton et al. | |
| 6,443,973 B1 | 9/2002 | Whitman | |
| 6,459,822 B1 | 10/2002 | Hathaway et al. | |
| 6,461,372 B1 | 10/2002 | Jensen et al. | |
| 6,471,637 B1 | 10/2002 | Green et al. | |
| 6,488,197 B1 | 12/2002 | Whitman | |
| 6,491,201 B1 | 12/2002 | Whitman | |
| 6,533,157 B1 | 3/2003 | Whitman | |
| 6,537,280 B2 | 3/2003 | Dinger et al. | |
| 6,610,066 B2 | 8/2003 | Dinger et al. | |
| 6,611,793 B1 | 8/2003 | Burnside et al. | |
| 6,645,218 B1 | 11/2003 | Cassidy et al. | |
| 6,654,999 B2 | 12/2003 | Stoddard et al. | |
| 6,698,643 B2 | 3/2004 | Whitman | |
| 6,699,177 B1 | 3/2004 | Wang et al. | |
| 6,716,233 B1 | 4/2004 | Whitman | |
| 6,743,240 B2 | 6/2004 | Smith et al. | |
| 6,783,533 B2 | 8/2004 | Green et al. | |
| 6,792,390 B1 | 9/2004 | Burnside et al. | |
| 6,793,652 B1 | 9/2004 | Whitman et al. | |
| 6,817,508 B1 | 11/2004 | Racenet et al. | |
| 6,830,174 B2 | 12/2004 | Hillstead et al. | |
| 6,846,308 B2 | 1/2005 | Whitman et al. | |
| 6,846,309 B2 | 1/2005 | Whitman et al. | |
| 6,849,071 B2 | 2/2005 | Whitman et al. | |
| 6,860,892 B1 | 3/2005 | Tanaka et al. | |
| 6,899,538 B2 | 5/2005 | Matoba | |
| 6,905,057 B2 | 6/2005 | Swayze et al. | |
| 6,959,852 B2 | 11/2005 | Shelton, IV et al. | |
| 6,964,363 B2 | 11/2005 | Wales et al. | |
| 6,981,628 B2 | 1/2006 | Wales | |
| 6,981,941 B2 | 1/2006 | Whitman et al. | |
| 6,986,451 B1 | 1/2006 | Mastri et al. | |
| 6,988,649 B2 | 1/2006 | Shelton, IV et al. | |
| 7,032,798 B2 | 4/2006 | Whitman et al. | |
| RE39,152 E | 6/2006 | Aust et al. | |
| 7,055,731 B2 | 6/2006 | Shelton, IV et al. | |
| 7,059,508 B2 | 6/2006 | Shelton, IV et al. | |
| 7,077,856 B2 | 7/2006 | Whitman | |
| 7,111,769 B2 | 9/2006 | Wales et al. | |
| 7,122,029 B2 | 10/2006 | Koop et al. | |
| 7,140,528 B2 | 11/2006 | Shelton, IV | |
| 7,141,049 B2 | 11/2006 | Stern et al. | |
| 7,143,923 B2 | 12/2006 | Shelton, IV et al. | |
| 7,143,925 B2 | 12/2006 | Shelton, IV et al. | |
| 7,143,926 B2 | 12/2006 | Shelton, IV et al. | |
| 7,147,138 B2 | 12/2006 | Shelton, IV | |
| 7,172,104 B2 | 2/2007 | Scirica et al. | |

(56) References Cited

U.S. PATENT DOCUMENTS

| | | | |
|---|---|---|---|
| 7,225,964 B2 | 6/2007 | Mastri et al. |
| 7,238,021 B1 | 7/2007 | Johnson |
| 7,246,734 B2 | 7/2007 | Shelton, IV |
| 7,252,660 B2 | 8/2007 | Kunz |
| 7,328,828 B2 | 2/2008 | Ortiz et al. |
| 7,364,061 B2 | 4/2008 | Swayze et al. |
| 7,380,695 B2 | 6/2008 | Doll et al. |
| 7,380,696 B2 | 6/2008 | Shelton, IV et al. |
| 7,404,508 B2 | 7/2008 | Smith et al. |
| 7,407,078 B2 | 8/2008 | Shelton, IV et al. |
| 7,416,101 B2 | 8/2008 | Shelton, IV et al. |
| 7,419,080 B2 | 9/2008 | Smith et al. |
| 7,422,139 B2 | 9/2008 | Shelton, IV et al. |
| 7,431,189 B2 | 10/2008 | Shelton, IV et al. |
| 7,441,684 B2 | 10/2008 | Shelton, IV et al. |
| 7,448,525 B2 | 11/2008 | Shelton, IV et al. |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,481,347 B2 | 1/2009 | Roy |
| 7,481,824 B2 | 1/2009 | Boudreaux et al. |
| 7,487,899 B2 | 2/2009 | Shelton, IV et al. |
| 7,549,564 B2 | 6/2009 | Boudreaux |
| 7,565,993 B2 | 7/2009 | Milliman et al. |
| 7,568,603 B2 | 8/2009 | Shelton, IV et al. |
| 7,575,144 B2 | 8/2009 | Ortiz et al. |
| 7,588,175 B2 | 9/2009 | Timm et al. |
| 7,588,176 B2 | 9/2009 | Timm et al. |
| 7,637,409 B2 | 12/2009 | Marczyk |
| 7,641,093 B2 | 1/2010 | Doll et al. |
| 7,644,848 B2 | 1/2010 | Swayze et al. |
| 7,670,334 B2 | 3/2010 | Hueil et al. |
| 7,673,780 B2 | 3/2010 | Shelton, IV et al. |
| 7,699,835 B2 | 4/2010 | Lee et al. |
| 7,721,931 B2 | 5/2010 | Shelton, IV et al. |
| 7,738,971 B2 | 6/2010 | Swayze et al. |
| 7,740,159 B2 | 6/2010 | Shelton, IV et al. |
| 7,743,960 B2 | 6/2010 | Whitman et al. |
| 7,758,613 B2 | 7/2010 | Whitman |
| 7,766,210 B2 | 8/2010 | Shelton, IV et al. |
| 7,770,773 B2 | 8/2010 | Whitman et al. |
| 7,770,775 B2 | 8/2010 | Shelton, IV et al. |
| 7,793,812 B2 | 9/2010 | Moore et al. |
| 7,799,039 B2 | 9/2010 | Shelton, IV et al. |
| 7,802,712 B2 | 9/2010 | Milliman et al. |
| 7,803,151 B2 | 9/2010 | Whitman |
| 7,822,458 B2 | 10/2010 | Webster, III et al. |
| 7,845,534 B2 | 12/2010 | Viola et al. |
| 7,845,537 B2 | 12/2010 | Shelton, IV et al. |
| 7,857,185 B2 | 12/2010 | Swayze et al. |
| 7,870,989 B2 | 1/2011 | Viola et al. |
| 7,900,805 B2 | 3/2011 | Shelton, IV et al. |
| 7,905,897 B2 | 3/2011 | Whitman et al. |
| 7,918,230 B2 | 4/2011 | Whitman et al. |
| 7,922,061 B2 | 4/2011 | Shelton, IV et al. |
| 7,922,719 B2 | 4/2011 | Ralph et al. |
| 7,947,034 B2 | 5/2011 | Whitman |
| 7,951,071 B2 | 5/2011 | Whitman et al. |
| 7,954,682 B2 | 6/2011 | Giordano et al. |
| 7,959,051 B2 | 6/2011 | Smith et al. |
| 7,963,433 B2 | 6/2011 | Whitman et al. |
| 7,967,178 B2 | 6/2011 | Scirica et al. |
| 7,967,179 B2 | 6/2011 | Olson et al. |
| 7,992,758 B2 | 8/2011 | Whitman et al. |
| 8,011,550 B2 | 9/2011 | Aranyi et al. |
| 8,016,178 B2 | 9/2011 | Olson et al. |
| 8,016,855 B2 | 9/2011 | Whitman et al. |
| 8,020,743 B2 | 9/2011 | Shelton, IV |
| 8,025,199 B2 | 9/2011 | Whitman et al. |
| 8,035,487 B2 | 10/2011 | Malackowski |
| 8,052,024 B2 | 11/2011 | Viola et al. |
| 8,056,787 B2 | 11/2011 | Boudreaux et al. |
| 8,114,118 B2 | 2/2012 | Knodel et al. |
| 8,127,975 B2 | 3/2012 | Olson et al. |
| 8,132,705 B2 | 3/2012 | Viola et al. |
| 8,152,516 B2 | 4/2012 | Harvey et al. |
| 8,157,150 B2 | 4/2012 | Viola et al. |
| 8,157,151 B2 | 4/2012 | Ingmanson et al. |
| 8,182,494 B1 | 5/2012 | Yencho et al. |
| 8,186,555 B2 | 5/2012 | Shelton, IV et al. |
| 8,186,587 B2 | 5/2012 | Zmood et al. |
| 8,220,367 B2 | 7/2012 | Hsu |
| 8,235,273 B2 | 8/2012 | Olson et al. |
| 8,241,322 B2 | 8/2012 | Whitman et al. |
| 8,272,554 B2 | 9/2012 | Whitman et al. |
| 8,292,150 B2 | 10/2012 | Bryant |
| 8,292,888 B2 | 10/2012 | Whitman |
| 8,303,581 B2 | 11/2012 | Arts et al. |
| 8,342,379 B2 | 1/2013 | Whitman et al. |
| 8,348,130 B2 | 1/2013 | Shah et al. |
| 8,348,855 B2 | 1/2013 | Hillely et al. |
| 8,353,440 B2 | 1/2013 | Whitman et al. |
| 8,357,144 B2 | 1/2013 | Whitman et al. |
| 8,365,633 B2 | 2/2013 | Simaan et al. |
| 8,365,972 B2 | 2/2013 | Aranyi et al. |
| 8,371,492 B2 | 2/2013 | Aranyi et al. |
| 8,372,057 B2 | 2/2013 | Cude et al. |
| 8,391,957 B2 | 3/2013 | Carlson et al. |
| 8,403,926 B2 | 3/2013 | Nobis et al. |
| 8,418,904 B2 | 4/2013 | Wenchell et al. |
| 8,424,739 B2 | 4/2013 | Racenet et al. |
| 8,454,585 B2 | 6/2013 | Whitman |
| 8,505,802 B2 | 8/2013 | Viola et al. |
| 8,517,241 B2 | 8/2013 | Nicholas et al. |
| 8,523,043 B2 | 9/2013 | Ullrich et al. |
| 8,551,076 B2 | 10/2013 | Duval et al. |
| 8,561,871 B2 | 10/2013 | Rajappa et al. |
| 8,561,874 B2 | 10/2013 | Scirica |
| 8,602,287 B2 | 12/2013 | Yates et al. |
| 8,623,000 B2 | 1/2014 | Humayun et al. |
| 8,627,995 B2 | 1/2014 | Smith et al. |
| 8,632,463 B2 | 1/2014 | Drinan et al. |
| 8,636,766 B2 | 1/2014 | Milliman et al. |
| 8,647,258 B2 | 2/2014 | Aranyi et al. |
| 8,652,121 B2 | 2/2014 | Quick et al. |
| 8,657,174 B2 | 2/2014 | Yates et al. |
| 8,657,177 B2 | 2/2014 | Scirica et al. |
| 8,672,206 B2 | 3/2014 | Aranyi et al. |
| 8,696,552 B2 | 4/2014 | Whitman |
| 8,708,213 B2 | 4/2014 | Shelton, IV et al. |
| 8,715,306 B2 | 5/2014 | Faller et al. |
| 8,752,749 B2 | 6/2014 | Moore et al. |
| 8,758,391 B2 | 6/2014 | Swayze et al. |
| 8,806,973 B2 | 8/2014 | Ross et al. |
| 8,808,311 B2 | 8/2014 | Heinrich et al. |
| 8,820,605 B2 | 9/2014 | Shelton, IV |
| 8,851,355 B2 | 10/2014 | Aranyi et al. |
| 8,858,571 B2 | 10/2014 | Shelton, IV et al. |
| 8,875,972 B2 | 11/2014 | Weisenburgh, II et al. |
| 8,888,762 B2 | 11/2014 | Whitman |
| 8,893,946 B2 | 11/2014 | Boudreaux et al. |
| 8,899,462 B2 | 12/2014 | Kostrzewski et al. |
| 8,905,289 B2 | 12/2014 | Patel et al. |
| 8,919,630 B2 | 12/2014 | Milliman |
| 8,931,680 B2 | 1/2015 | Milliman |
| 8,939,344 B2 | 1/2015 | Olson et al. |
| 8,950,646 B2 | 2/2015 | Viola |
| 8,960,519 B2 | 2/2015 | Whitman et al. |
| 8,961,396 B2 | 2/2015 | Azarbarzin et al. |
| 8,967,443 B2 | 3/2015 | McCuen |
| 8,968,276 B2 | 3/2015 | Zemlok et al. |
| 8,968,337 B2 | 3/2015 | Whitfield et al. |
| 8,992,422 B2 | 3/2015 | Spivey et al. |
| 9,016,545 B2 | 4/2015 | Aranyi et al. |
| 9,023,014 B2 | 5/2015 | Chowaniec et al. |
| 9,033,868 B2 | 5/2015 | Whitman et al. |
| 9,055,943 B2 | 6/2015 | Zemlok et al. |
| 9,064,653 B2 | 6/2015 | Prest et al. |
| 9,072,515 B2 | 7/2015 | Hall et al. |
| 9,113,847 B2 | 8/2015 | Whitman et al. |
| 9,113,875 B2 | 8/2015 | Viola et al. |
| 9,113,876 B2 | 8/2015 | Zemlok et al. |
| 9,113,899 B2 | 8/2015 | Garrison et al. |
| 9,216,013 B2 | 12/2015 | Scirica et al. |

(56) References Cited

U.S. PATENT DOCUMENTS

| | | |
|---|---|---|
| 9,282,961 B2 | 3/2016 | Whitman et al. |
| 9,282,963 B2 | 3/2016 | Bryant |
| 9,295,522 B2 | 3/2016 | Kostrzewski |
| 9,307,986 B2 | 4/2016 | Hall et al. |
| 2001/0031975 A1 | 10/2001 | Whitman et al. |
| 2002/0049454 A1 | 4/2002 | Whitman et al. |
| 2002/0165541 A1 | 11/2002 | Whitman |
| 2003/0038938 A1 | 2/2003 | Jung et al. |
| 2003/0130677 A1 | 7/2003 | Whitman et al. |
| 2003/0165794 A1 | 9/2003 | Matoba |
| 2004/0111012 A1 | 6/2004 | Whitman |
| 2004/0133189 A1 | 7/2004 | Sakurai |
| 2004/0153124 A1 | 8/2004 | Whitman |
| 2004/0176751 A1 | 9/2004 | Weitzner et al. |
| 2004/0193146 A1 | 9/2004 | Lee et al. |
| 2005/0125027 A1 | 6/2005 | Knodel et al. |
| 2005/0131442 A1 | 6/2005 | Yachia et al. |
| 2005/0187576 A1 | 8/2005 | Whitman et al. |
| 2006/0142656 A1 | 6/2006 | Malackowski et al. |
| 2006/0142740 A1 | 6/2006 | Sherman et al. |
| 2006/0142744 A1 | 6/2006 | Boutoussov |
| 2006/0259073 A1 | 11/2006 | Miyamoto et al. |
| 2006/0278680 A1 | 12/2006 | Viola et al. |
| 2006/0284730 A1 | 12/2006 | Schmid et al. |
| 2007/0023476 A1 | 2/2007 | Whitman et al. |
| 2007/0023477 A1 | 2/2007 | Whitman et al. |
| 2007/0029363 A1 | 2/2007 | Popov |
| 2007/0055219 A1 | 3/2007 | Whitman et al. |
| 2007/0084897 A1 | 4/2007 | Shelton et al. |
| 2007/0102472 A1 | 5/2007 | Shelton |
| 2007/0152014 A1 | 7/2007 | Gillum et al. |
| 2007/0175947 A1 | 8/2007 | Ortiz et al. |
| 2007/0175949 A1 | 8/2007 | Shelton et al. |
| 2007/0175950 A1 | 8/2007 | Shelton et al. |
| 2007/0175951 A1 | 8/2007 | Shelton et al. |
| 2007/0175955 A1 | 8/2007 | Shelton et al. |
| 2007/0175961 A1 | 8/2007 | Shelton et al. |
| 2007/0270784 A1 | 11/2007 | Smith et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0058801 A1 | 3/2008 | Taylor et al. |
| 2008/0105730 A1 | 5/2008 | Racenet et al. |
| 2008/0109012 A1 | 5/2008 | Falco et al. |
| 2008/0110958 A1 | 5/2008 | McKenna et al. |
| 2008/0147089 A1 | 6/2008 | Loh et al. |
| 2008/0167736 A1 | 7/2008 | Swayze et al. |
| 2008/0185419 A1 | 8/2008 | Smith et al. |
| 2008/0188841 A1 | 8/2008 | Tomasello et al. |
| 2008/0197167 A1 | 8/2008 | Viola et al. |
| 2008/0208195 A1 | 8/2008 | Shores et al. |
| 2008/0237296 A1 | 10/2008 | Boudreaux et al. |
| 2008/0251561 A1 | 10/2008 | Eades et al. |
| 2008/0255413 A1 | 10/2008 | Zemlok et al. |
| 2008/0255607 A1 | 10/2008 | Zemlok |
| 2008/0262654 A1 | 10/2008 | Omori et al. |
| 2008/0308603 A1 | 12/2008 | Shelton et al. |
| 2009/0012533 A1 | 1/2009 | Barbagli et al. |
| 2009/0090763 A1 | 4/2009 | Zemlok et al. |
| 2009/0099876 A1 | 4/2009 | Whitman |
| 2009/0101692 A1 | 4/2009 | Whitman et al. |
| 2009/0138006 A1 | 5/2009 | Bales et al. |
| 2009/0145947 A1 | 6/2009 | Scirica et al. |
| 2009/0171147 A1 | 7/2009 | Lee et al. |
| 2009/0179063 A1 | 7/2009 | Milliman et al. |
| 2009/0182193 A1 | 7/2009 | Whitman et al. |
| 2009/0209990 A1 | 8/2009 | Yates et al. |
| 2009/0254094 A1 | 10/2009 | Knapp et al. |
| 2009/0299141 A1 | 12/2009 | Downey et al. |
| 2010/0023022 A1 | 1/2010 | Zeiner et al. |
| 2010/0069942 A1 | 3/2010 | Shelton, IV |
| 2010/0193568 A1 | 8/2010 | Scheib et al. |
| 2010/0211053 A1 | 8/2010 | Ross et al. |
| 2010/0225073 A1 | 9/2010 | Porter et al. |
| 2011/0006101 A1 | 1/2011 | Hall et al. |
| 2011/0017801 A1 | 1/2011 | Zemlok et al. |
| 2011/0071508 A1 | 3/2011 | Duval et al. |
| 2011/0077673 A1 | 3/2011 | Grubac et al. |
| 2011/0121049 A1 | 5/2011 | Malinouskas et al. |
| 2011/0125138 A1 | 5/2011 | Malinouskas et al. |
| 2011/0139851 A1 | 6/2011 | McCuen |
| 2011/0155783 A1 | 6/2011 | Rajappa et al. |
| 2011/0155786 A1 | 6/2011 | Shelton, IV |
| 2011/0172648 A1 | 7/2011 | Jeong |
| 2011/0174099 A1 | 7/2011 | Ross et al. |
| 2011/0184245 A1 | 7/2011 | Xia et al. |
| 2011/0204119 A1 | 8/2011 | McCuen |
| 2011/0218522 A1 | 9/2011 | Whitman |
| 2011/0253765 A1 | 10/2011 | Nicholas et al. |
| 2011/0276057 A1 | 11/2011 | Conlon et al. |
| 2011/0290854 A1 | 12/2011 | Timm et al. |
| 2011/0295242 A1 | 12/2011 | Spivey et al. |
| 2011/0295269 A1 | 12/2011 | Swensgard et al. |
| 2012/0000962 A1 | 1/2012 | Racenet et al. |
| 2012/0074199 A1 | 3/2012 | Olson et al. |
| 2012/0089131 A1 | 4/2012 | Zemlok et al. |
| 2012/0104071 A1 | 5/2012 | Bryant |
| 2012/0116368 A1 | 5/2012 | Viola |
| 2012/0143002 A1 | 6/2012 | Aranyi et al. |
| 2012/0172924 A1 | 7/2012 | Allen, IV |
| 2012/0211542 A1 | 8/2012 | Racenet |
| 2012/0223121 A1 | 9/2012 | Viola et al. |
| 2012/0245428 A1 | 9/2012 | Smith et al. |
| 2012/0253329 A1 | 10/2012 | Zemlok et al. |
| 2012/0310220 A1 | 12/2012 | Malkowski et al. |
| 2012/0323226 A1 | 12/2012 | Chowaniec et al. |
| 2012/0330285 A1 | 12/2012 | Hartoumbekis et al. |
| 2013/0018361 A1 | 1/2013 | Bryant |
| 2013/0093149 A1 | 4/2013 | Saur et al. |
| 2013/0098966 A1 | 4/2013 | Kostrzewski et al. |
| 2013/0098968 A1 | 4/2013 | Aranyi et al. |
| 2013/0098969 A1 | 4/2013 | Scirica et al. |
| 2013/0181035 A1 | 7/2013 | Milliman |
| 2013/0184704 A1 | 7/2013 | Beardsley et al. |
| 2013/0214025 A1 | 8/2013 | Zemlok et al. |
| 2013/0240596 A1 | 9/2013 | Whitman |
| 2013/0274722 A1 | 10/2013 | Kostrzewski et al. |
| 2013/0282052 A1 | 10/2013 | Aranyi et al. |
| 2013/0292451 A1 | 11/2013 | Viola et al. |
| 2013/0313304 A1 | 11/2013 | Shelton, IV et al. |
| 2013/0317486 A1 | 11/2013 | Nicholas et al. |
| 2013/0319706 A1 | 12/2013 | Nicholas et al. |
| 2013/0324978 A1 | 12/2013 | Nicholas et al. |
| 2013/0324979 A1 | 12/2013 | Nicholas et al. |
| 2013/0334281 A1 | 12/2013 | Williams |
| 2014/0012236 A1 | 1/2014 | Williams et al. |
| 2014/0012237 A1 | 1/2014 | Pribanic et al. |
| 2014/0012289 A1 | 1/2014 | Snow et al. |
| 2014/0025046 A1 | 1/2014 | Williams et al. |
| 2014/0110455 A1 | 4/2014 | Ingmanson et al. |
| 2014/0207125 A1 | 7/2014 | Applegate et al. |
| 2014/0207182 A1 | 7/2014 | Zergiebel et al. |
| 2014/0207185 A1 | 7/2014 | Goble et al. |
| 2014/0236173 A1 | 8/2014 | Scirica et al. |
| 2014/0236174 A1 | 8/2014 | Williams et al. |
| 2014/0276932 A1 | 9/2014 | Williams et al. |
| 2014/0299647 A1 | 10/2014 | Scirica et al. |
| 2014/0303668 A1 | 10/2014 | Nicholas et al. |
| 2014/0358129 A1 | 12/2014 | Zergiebel et al. |
| 2014/0361068 A1 | 12/2014 | Aranyi et al. |
| 2014/0365235 A1 | 12/2014 | DeBoer et al. |
| 2014/0373652 A1 | 12/2014 | Zergiebel et al. |
| 2015/0014392 A1 | 1/2015 | Williams et al. |
| 2015/0048144 A1 | 2/2015 | Whitman |
| 2015/0076205 A1 | 3/2015 | Zergiebel |
| 2015/0080912 A1 | 3/2015 | Sapre |
| 2015/0112381 A1 | 4/2015 | Richard |
| 2015/0122870 A1 | 5/2015 | Zemlok et al. |
| 2015/0133224 A1 | 5/2015 | Whitman et al. |
| 2015/0133957 A1 | 5/2015 | Kostrzewski |
| 2015/0150547 A1 | 6/2015 | Ingmanson et al. |
| 2015/0150574 A1 | 6/2015 | Richard et al. |
| 2015/0157320 A1 | 6/2015 | Zergiebel et al. |

(56) References Cited

U.S. PATENT DOCUMENTS

| | | |
|---|---|---|
| 2015/0157321 A1 | 6/2015 | Zergiebel et al. |
| 2015/0164502 A1 | 6/2015 | Richard et al. |
| 2015/0201931 A1 | 7/2015 | Zergiebel et al. |
| 2015/0272577 A1 | 10/2015 | Zemlok et al. |
| 2015/0297199 A1 | 10/2015 | Nicholas et al. |
| 2015/0303996 A1 | 10/2015 | Calderoni |
| 2015/0320420 A1 | 11/2015 | Penna et al. |
| 2015/0327850 A1 | 11/2015 | Kostrzewski |
| 2015/0342601 A1 | 12/2015 | Williams et al. |
| 2015/0342603 A1 | 12/2015 | Zergiebel et al. |
| 2015/0374366 A1 | 12/2015 | Zergiebel et al. |
| 2015/0374370 A1 | 12/2015 | Zergiebel et al. |
| 2015/0374371 A1 | 12/2015 | Richard et al. |
| 2015/0374372 A1 | 12/2015 | Zergiebel et al. |
| 2015/0374449 A1 | 12/2015 | Chowaniec et al. |
| 2015/0380187 A1 | 12/2015 | Zergiebel et al. |
| 2016/0095585 A2 | 4/2016 | Zergiebel et al. |
| 2016/0095596 A1 | 4/2016 | Scirica et al. |
| 2016/0106406 A1 | 4/2016 | Cabrera et al. |
| 2016/0113648 A1 | 4/2016 | Zergiebel et al. |
| 2016/0113649 A1 | 4/2016 | Zergiebel et al. |

FOREIGN PATENT DOCUMENTS

| | | | |
|---|---|---|---|
| CA | 2824590 | A1 | 4/2014 |
| CN | 101856251 | A | 10/2010 |
| CN | 102247182 | A | 11/2011 |
| DE | 102008053842 | A1 | 5/2010 |
| EP | 0634144 | A1 | 1/1995 |
| EP | 0648476 | A1 | 4/1995 |
| EP | 0686374 | A2 | 12/1995 |
| EP | 0705571 | A1 | 4/1996 |
| EP | 1690502 | A1 | 8/2006 |
| EP | 1723913 | A1 | 11/2006 |
| EP | 1736112 | A1 | 12/2006 |
| EP | 1759652 | A2 | 3/2007 |
| EP | 1 769 754 | A1 | 4/2007 |
| EP | 1772105 | A1 | 4/2007 |
| EP | 1 813 199 | A1 | 8/2007 |
| EP | 1 813 203 | A2 | 8/2007 |
| EP | 1813211 | A2 | 8/2007 |
| EP | 1908412 | A2 | 4/2008 |
| EP | 1917929 | A1 | 5/2008 |
| EP | 1943954 | A2 | 7/2008 |
| EP | 1943956 | A2 | 7/2008 |
| EP | 1943958 | A1 | 7/2008 |
| EP | 1943976 | A2 | 7/2008 |
| EP | 1952769 | A2 | 8/2008 |
| EP | 2005898 | A2 | 12/2008 |
| EP | 2027819 | A1 | 2/2009 |
| EP | 2044890 | A1 | 4/2009 |
| EP | 2055243 | A2 | 5/2009 |
| EP | 2090247 | A1 | 8/2009 |
| EP | 2098170 | A2 | 9/2009 |
| EP | 2100561 | A2 | 9/2009 |
| EP | 2100562 | A2 | 9/2009 |
| EP | 2165664 | A2 | 3/2010 |
| EP | 2 236 098 | A2 | 10/2010 |
| EP | 2245994 | A1 | 11/2010 |
| EP | 2263568 | A2 | 12/2010 |
| EP | 2272443 | A1 | 1/2011 |
| EP | 2316345 | A1 | 5/2011 |
| EP | 2324776 | A2 | 5/2011 |
| EP | 2329773 | A1 | 6/2011 |
| EP | 2333509 | A1 | 6/2011 |
| EP | 2377472 | A1 | 10/2011 |
| EP | 2 462 880 | A2 | 6/2012 |
| EP | 2462878 | A1 | 6/2012 |
| EP | 2491872 | A1 | 8/2012 |
| EP | 2586382 | A2 | 5/2013 |
| EP | 2606834 | A2 | 6/2013 |
| EP | 2668910 | A2 | 12/2013 |
| EP | 2676615 | A2 | 12/2013 |
| EP | 2815705 | A1 | 12/2014 |
| ES | 2333509 | A1 | 2/2010 |
| FR | 2861574 | A1 | 5/2005 |
| JP | 08-038488 | | 2/1996 |
| JP | 2005-125075 | A | 5/2005 |
| JP | 2005253632 | A | 9/2005 |
| JP | 2009213903 | A | 9/2009 |
| JP | 201183618 | A | 4/2011 |
| JP | 2012505046 | A | 3/2012 |
| KR | 20120022521 | A | 3/2012 |
| WO | 99/15086 | A1 | 4/1999 |
| WO | 0072760 | A1 | 12/2000 |
| WO | 0072765 | A1 | 12/2000 |
| WO | 03/000138 | A2 | 1/2003 |
| WO | 03/026511 | A1 | 4/2003 |
| WO | 03/030743 | A2 | 4/2003 |
| WO | 03065916 | A1 | 8/2003 |
| WO | 03077769 | A1 | 9/2003 |
| WO | 03/090630 | A3 | 4/2004 |
| WO | 2004/107989 | A1 | 12/2004 |
| WO | 2006/042210 | A2 | 4/2006 |
| WO | 2007/014355 | A2 | 2/2007 |
| WO | 2007016290 | A2 | 2/2007 |
| WO | 2007/026354 | A1 | 3/2007 |
| WO | 2007137304 | A2 | 11/2007 |
| WO | 2008/131362 | A2 | 10/2008 |
| WO | 2008/133956 | A2 | 11/2008 |
| WO | 2009/039506 | A1 | 3/2009 |
| WO | 2009/132359 | A2 | 10/2009 |
| WO | 2009/143092 | A1 | 11/2009 |
| WO | 2009/149234 | A1 | 12/2009 |
| WO | 2011/108840 | A2 | 9/2011 |
| WO | 2012/040984 | A1 | 4/2012 |

OTHER PUBLICATIONS

Japanese Office Action corresponding to International Application No. JP 2011-084092 dated Jan. 14, 2016.
Extended European Search Report corresponding to International Application No. EP 12 19 7970.2 dated Jan. 28, 2016.
Chinese Office Action corresponding to International Application No. CN 201210560638.1 dated Oct. 21, 2015.
European Office Action corresponding to International Application No. EP 14 15 9056.2 dated Oct. 26, 2015.
Australian Examination Report No. 1 corresponding to International Application No. AU 2015200153 dated Dec. 11, 2015.
Australian Examination Report No. 1 corresponding to International Application No. AU 2014204542 dated Jan. 7, 2016.
Chinese Office Action corresponding to International Application No. CN 201310125449.6 dated Feb. 3, 2016.
Extended European Search Report corresponding to International Application No. EP 15 19 0245.9 dated Jan. 28, 2016.
Extended European Search Report corresponding to International Application No. EP 15 16 7793.7 dated Apr. 5, 2016.
European Office Action corresponding to International Application No. EP 14 18 4882.0 dated Apr. 25, 2016.
Extended European Search Report corresponding to International Application No. EP 14 19 6704.2 dated Sep. 24, 2015.
International Search Report and Written Opinion corresponding to Int'l Appln. No. PCT/US2015/051837, dated Dec. 21, 2015.
Extended European Search Report corresponding to International Application No. EP 14 19 7563.1 dated Aug. 5, 2015.
Partial European Search Report corresponding to International Application No. EP 15 19 0643.5 dated Feb. 26, 2016.
Extended European Search Report corresponding to International Application No. EP 15 16 6899.3 dated Feb. 3, 2016.
Extended European Search Report corresponding to International Application No. EP 14 19 9783.3 dated Dec. 22, 2015.
Extended European Search Report corresponding to International Application No. EP 15 17 3807.7 dated Nov. 24, 2015.
Extended European Search Report corresponding to International Application No. EP 15 19 0760.7 dated Apr. 1, 2016.
Extended European Search Report corresponding to International Application No. EP 15 17 3803.6 dated Nov. 24, 2015.
Extended European Search Report corresponding to International Application No. EP 15 17 3804.4 dated Nov. 24, 2015.

(56) References Cited

OTHER PUBLICATIONS

Extended European Search Report corresponding to International Application No. EP 15 18 8539.9 dated Feb. 17, 2016.
Extended European Search Report corresponding to International Application No. EP 15 17 3910.9 dated Nov. 13, 2015.
European Office Action corresponding to International Application No. EP 14 15 2236.7 dated Aug. 11, 2015.
Extended European Search Report corresponding to International Application No. EP 15 18 4915.5 dated Jan. 5, 2016.
Chinese Office Action dated Mar. 1, 2017 issued in corresponding Chinese Application No. 2014100555823.
Japanese Office Action dated Oct. 30, 2017 issued in correponding Japanese Application No. 2014-027259.
Chinese Office Action dated Sep. 4, 2017 issued in corresponding Chinese Application No. 2014100555823.
Partial European Search Report corresponding to EP 12 18 6177.7, completed Jan. 30, 2013 and dated Feb. 12, 2013; (6 pp.).
International Search Report corresponding to PCT/US2005/027266, completed May 30, 2008 and dated Jun. 18, 2008; (2 pp.).
Extended European Search Report corresponding to EP 11 25 0771.0, completed Feb. 7, 2012 and dated Feb. 17, 2012; (3 pp.).
Extended European Search Report corresponding to EP 11 25 0462.6, completed Jul. 20, 2011 and dated Jul. 28, 2011; (6 pp.).
Extended European Search Report corresponding to EP 11 15 2266.0, completed Jul. 15, 2011 and dated Jul. 28, 2011; (3 pp.).
Extended European Search Report corresponding to EP 10 25 1968.3, completed on Jul. 4, 2011 and dated Jul. 14, 2011; (12 pp.).
Extended European Search Report corresponding to EP 10 25 0228.3, completed May 20, 2010 and dated Jun. 1, 2010; (6 pp.).
Extended European Search Report corresponding to EP 08 25 3184.9, completed Feb. 12, 2009 and dated Feb. 27, 2009; (3 pp.).
Extended European Search Report corresponding to EP 08 25 2703.7, completed Oct. 23, 2008 and dated Oct. 31, 2008; (7 pp.).
Extended European Search Report corresponding to EP 06 78 8914.7, completed May 3, 2012 and dated May 11, 2012; (8 pp.).
European Search Report No. 14155329.7 dated Oct. 7, 2014.
Extended European Search Report corresponding to EP No. 11 17 8021.9, dated Jun. 4, 2013; (3 pp).
Extended European Search Report corresponding to EP No. 13 16 3033.7, completed Jun. 27, 2013 and dated Jul. 15, 2013; (8 pp).
Extended European Search Report corresponding to EP No. 12 18 6177.7, completed Aug. 14, 2013 and dated Aug. 23, 2013; (8 pp).
Partial European Search Report corresponding to EP No. 13 17 1742.3, completed Sep. 17, 2013 and dated Sep. 25, 2013; (8 pp).
Partial European Search Report corresponding to EP No. 13 17 2400.7, completed Sep. 18, 2013 and dated Oct. 1, 2013; (7 pp).
Extended European Search Report corresponding to EP No. 13 17 5475.6, completed Sep. 23, 2013 and dated Oct. 1, 2013; (8 pp).
Extended European Search Report corresponding to EP No. 13 17 5478.0, completed Sep. 24, 2013 and dated Oct. 2, 2013; (6 pp).
Extended European Search Report corresponding to EP No. 13 17 5479.8, completed Sep. 27, 2013 and dated Oct. 10, 2013; (7 pp).
Partial Extended European Search Report corresponding to EP 13 17 5477.2, completed Oct. 7, 2013 and dated Oct. 15, 2013; (7 pp).
Extended European Search Report corresponding to EP No. 08 25 2703.7, completed Oct. 23, 2008 and dated Oct. 31, 2008; (7 pp).
European Search Report corresponding to EP 10 25 2037.6; completed Mar. 1, 2011 and dated Mar. 9, 2011; 3 pages.
European search Report from Appl. No. 13177163.6 dated Nov. 15, 2013. (8 pp).
Extended European Search Report from EP Application No. 13172400.7 dated Jan. 21, 2014.
Extended European Search Report from EP Application No. 13189026.1 dated Jan. 31, 2014.
Extended European Search Report from Application No. EP 13177163.6 dated Feb. 6, 2014.
Extended European Search Report from Application No. EP 13175477.2 dated Feb. 6, 2014.
Extended European Search Report from Application No. EP 13169998.5 dated Feb. 24, 2014.
Extended European Search Report corresponding to EP 13176805.3, dated Nov. 4, 2013.
Extended European Search Report from Application No. EP 13171742.3 dated Jan. 3, 2014.
European Examination Report dated Jun. 15, 2015 from Application No. EP 14155329.7.
Extended European Search Report corresponding to counterpart International Application No. EP 14 18 4882.0 dated May 12, 2015.
Canadian Office Action corresponding to counterpart International Application No. CA 2640399 dated May 7, 2015.
Japanese 2015 Office Action corresponding to counterpart International Application No. JP 2011-197365 dated Mar. 23, 2015.
Japanese Office Action corresponding to counterpart International Application No. JP 2011-084092 dated May 20, 2015.
Japanese Office Action corresponding to counterpart International Application No. JP 2014-148482 dated Jun. 2, 2015.
Extended European Search Report corresponding to counterpart International Application No. EP 14 18 9358.6 dated Jul. 8, 2015.
Extended European Search Report corresponding to counterpart International Application No. EP 14 19 6148.2 dated Apr. 23, 2015.
Partial European Search Report corresponding to counterpart International Application No. EP 14 19 6704.2 dated May 11, 2015.
Australian Office Action corresponding to counterpart International Application No. AU 2010241367 dated Aug. 20, 2015.
Partial European Search Report corresponding to counterpart International Application No. EP 14 19 9783.3 dated Sep. 3, 2015.
Extended European Search Report corresponding to counterpart International Application No. EP 15 16 9962.6 dated Sep. 14, 2015.
Australian Examination Report dated Jun. 29, 2017 issued in corresponding Australian Application No. 2014200185.
Japanese Notice of Allowance dated Feb. 13, 2018 issued in corresponding Japanese Application No. 2014-027259. (Summary only).

APPARATUS FOR ENDOSCOPIC PROCEDURES

CROSS-REFERENCE TO RELATED APPLICATIONS

The present application is a continuation application of U.S. patent application Ser. No. 13/769,414, filed on Feb. 18, 2013, the entire contents of which is incorporated by reference herein.

BACKGROUND

1. Technical Field

The present disclosure relates to surgical apparatus, devices and/or systems for performing endoscopic surgical procedures and methods of use thereof. More specifically, the present disclosure relates to electromechanical, hand-held surgical apparatus, devices and/or systems configured for use with removable disposable loading units and/or single use loading units for clamping, cutting and/or stapling tissue.

2. Background of Related Art

A number of surgical device manufacturers have developed product lines with proprietary drive systems for operating and/or manipulating electromechanical surgical devices. In many instances the electromechanical surgical devices include a handle assembly, which is reusable, and disposable loading units and/or single use loading units or the like that are selectively connected to the handle assembly prior to use and then disconnected from the handle assembly following use in order to be disposed of or in some instances sterilized for re-use.

Many of these electromechanical surgical devices are relatively expensive to manufacture, purchase and/or operate. There is a constant desire by manufactures and end users to develop electromechanical surgical devices that are relatively inexpensive to manufacture, purchase and/or operate yet still provide a large degree of operability.

Accordingly, a need exists for electromechanical surgical apparatus, devices and/or systems that are relatively economical from the development and manufacturing stages, to the selling/purchase stages, to the storing/shipping stages, to the use/operation stages, and on to the disposal and/or re-use stages while still providing an end user with a high degree of operability.

SUMMARY

The present disclosure relates to electromechanical, hand-held surgical apparatus, devices and/or systems configured for use with removable disposable loading units and/or single use loading units for clamping, cutting and/or stapling tissue.

According to an aspect of the present disclosure, an electromechanical surgical device is provided and includes an end effector configured to perform at least one function; and a shaft assembly. The a shaft assembly including a proximal neck housing supported at a distal end of the outer tube; a distal neck housing pivotally connected to the proximal neck housing, wherein a distal end of the distal neck housing is configured and adapted for operative connection with the end effector; a flexible drive cable extending through the shaft assembly, the proximal neck housing and the distal neck housing; and an articulation rod at least partially slidably supported in the distal neck housing. The articulation rod includes a distal end; and a proximal end operatively connected to a rotatable drive shaft; wherein the articulation rod is off set a radial distance from the central longitudinal axis of the shaft assembly. The shaft assembly also includes an articulation link having a proximal end pivotally connected to the distal end of the articulation rod, and a distal end pivotally connected to the distal neck housing.

In use, actuation of the rotatable drive shaft of the hand-held surgical device that is connected to the articulation rod causes the articulation rod to axially translate; and axial translation of the articulation rod causes the distal neck housing to pivot off axis relative to the proximal neck housing.

A pivot axis between the proximal neck housing and the distal neck housing may traverse a central longitudinal axis. The distal neck housing may pivot in a single direction relative to the proximal neck housing.

The distal neck housing may define a proximal chamfered surface, and the proximal neck housing may define a distal chamfered surface, whereby the distal neck housing is pivotable by about 90° relative to the central longitudinal axis.

The flexible drive cable may include a distal end; and a proximal end operatively connected to a respective rotatable drive shaft of a hand-held surgical device; wherein the flexible drive cable is off set a radial distance from the central longitudinal axis of the outer tube.

The shaft assembly may include a hub rotatably supported at a distal end of the distal neck housing; and a rotation hub rotatably supported in the hub, wherein the rotation hub is connected to the distal end of the flexible drive cable, and wherein the rotation hub is configured to selectively connect with a rotatable drive axle of the end effector.

The flexible drive cable may be sheathed in a coil spring.

The distal end of the flexible drive cable may rotate about a central longitudinal axis together with a rotation of the rotation hub relative to the central longitudinal axis.

The rotation hub may be rotatable by about +/−90°.

A pivot axis between the proximal neck housing and the distal neck housing may traverse the central longitudinal axis.

The distal neck housing may pivot in a single direction relative to the proximal neck housing.

The distal neck housing may define a proximal chamfered surface, and wherein the proximal neck housing may define a distal chamfered surface, whereby the distal neck housing is pivotable by about 90° relative to the central longitudinal axis.

The shaft assembly may include a flexible drive cable rotatably supported in an outer tube. The flexible drive cable may include a distal end; and a proximal end operatively connected to a respective rotatable drive shaft of the hand-held surgical device; wherein the flexible drive cable is off set a radial distance from the central longitudinal axis of the outer tube.

According to another aspect of the present disclosure, an electromechanical surgical system is provided and includes a hand-held surgical device including a device housing defining a connecting portion for selectively connecting with an adapter assembly and at least one rotatable drive shaft; an end effector configured to perform at least one function; and a shaft assembly for selectively interconnecting the end effector and the surgical device. The shaft assembly includes a proximal neck housing supported at a distal end of the outer tube; a distal neck housing pivotally connected to the proximal neck housing, wherein a distal end of the distal neck housing is configured and adapted for operative connection with the end effector; and a flexible drive cable rotatably supported in the outer tube. The flexible drive cable includes a distal end; and a proximal end operatively connected to a respective rotatable drive shaft of the hand-held surgical device; wherein the flexible drive cable is off set a radial distance from the central longitudinal axis of the outer tube.

The shaft assembly further includes a hub rotatably supported at a distal end of the distal neck housing; and a rotation hub rotatably supported in the hub, wherein the rotation hub is connected to the distal end of the flexible drive cable. The rotation hub is configured to selectively connect with a rotatable drive axle of the end effector.

The flexible drive cable may be sheathed in a coil spring.

The distal end of the flexible drive cable may rotate about the central longitudinal axis together with a rotation of the rotation hub relative to the central longitudinal axis.

The rotation hub may be rotatable by about +/−90°.

A pivot axis between the proximal neck housing and the distal neck housing may traverse the central longitudinal axis. The distal neck housing may pivot in a single direction relative to the proximal neck housing.

The distal neck housing may define a proximal chamfered surface, and wherein the proximal neck housing may define a distal chamfered surface, whereby the distal neck housing is pivotable by about 90° relative to the central longitudinal axis.

The shaft assembly may further include an articulation rod at least partially slidably supported in the distal neck housing. The articulation rod may include a distal end; and a proximal end operatively connected to a respective rotatable drive shaft of the hand-held surgical device; wherein the articulation rod is off set a radial distance from the central longitudinal axis of the outer tube. The shaft assembly may include an articulation link having a proximal end pivotally connected to the distal end of the articulation rod, and a distal end pivotally connected to the distal neck housing.

In use, actuation of the rotatable drive shaft of the hand-held surgical device, that is connected to the articulation rod, may cause the articulation rod to axially translate. In use, axial translation of the articulation rod may cause the distal neck housing to pivot off axis relative to the proximal neck housing.

According to a further aspect of the present disclosure, a shaft assembly for interconnecting at least one rotatable drive shaft of a hand-held electromechanical surgical device, and an end effector actuatable by an axial drive force is provided. The shaft assembly includes a shaft coupling assembly configured and adapted for selective connection to the connecting portion of the surgical device and to be in operative communication with each of the at least one rotatable drive shaft of the surgical device; an outer tube having a proximal end supported by the shaft coupling assembly, the outer tube defining a central longitudinal axis; a proximal neck housing supported at a distal end of the outer tube; a distal neck housing pivotally connected to the proximal neck housing, wherein a distal end of the distal neck housing is configured and adapted for operative connection with the end effector; a flexible drive cable rotatably supported in the outer tube; an articulation rod at least partially slidably supported in the distal neck housing; and an articulation link having a proximal end pivotally connected to the distal end of the articulation rod, and a distal end pivotally connected to the distal neck housing. Actuation of the rotatable drive shaft of the hand-held surgical device, that is connected to the articulation rod, causes the articulation rod to axially translate. Axial translation of the articulation rod causes the distal neck housing to pivot off axis relative to the proximal neck housing.

A pivot axis between the proximal neck housing and the distal neck housing may traverse the central longitudinal axis. The distal neck housing may pivot in a single direction relative to the proximal neck housing.

The distal neck housing may define a proximal chamfered surface, and wherein the proximal neck housing may define a distal chamfered surface, whereby the distal neck housing is pivotable by about 90° relative to the central longitudinal axis.

The shaft assembly may include a flexible drive cable rotatably supported in the outer tube. The flexible drive cable may include a distal end; and a proximal end operatively connected to a respective rotatable drive shaft of the hand-held surgical device; wherein the flexible drive cable is off set a radial distance from the central longitudinal axis of the outer tube.

The shaft assembly may further include a hub rotatably supported at a distal end of the distal neck housing; a rotation hub rotatably supported in the hub, wherein the rotation hub is connected to the distal end of the flexible drive cable. The rotation hub may be configured to selectively connect with a rotatable drive axle of the end effector.

The flexible drive cable may be sheathed in a coil spring.

The distal end of the flexible drive cable may rotate about the central longitudinal axis together with a rotation of the rotation hub relative to the central longitudinal axis.

The rotation hub may be rotatable by about +/−90°.

A pivot axis between the proximal neck housing and the distal neck housing may traverse the central longitudinal axis. The distal neck housing may pivot in a single direction relative to the proximal neck housing.

The distal neck housing may define a proximal chamfered surface, and wherein the proximal neck housing may define a distal chamfered surface, whereby the distal neck housing is pivotable by about 90° relative to the central longitudinal axis.

The shaft assembly may further include a flexible drive cable rotatably supported in the outer tube. The flexible drive cable may include a distal end; and a proximal end operatively connected to a respective rotatable drive shaft of the hand-held surgical device; wherein the flexible drive cable is off set a radial distance from the central longitudinal axis of the outer tube.

Further details and aspects of exemplary embodiments of the present invention are described in more detail below with reference to the appended figures.

BRIEF DESCRIPTION OF THE DRAWINGS

Embodiments of the present disclosure are described herein with reference to the accompanying drawings, wherein:

FIG. 5A is an enlarged view of the indicated area of detail of FIG. 5;

DETAILED DESCRIPTION OF EMBODIMENTS

Figure 1:
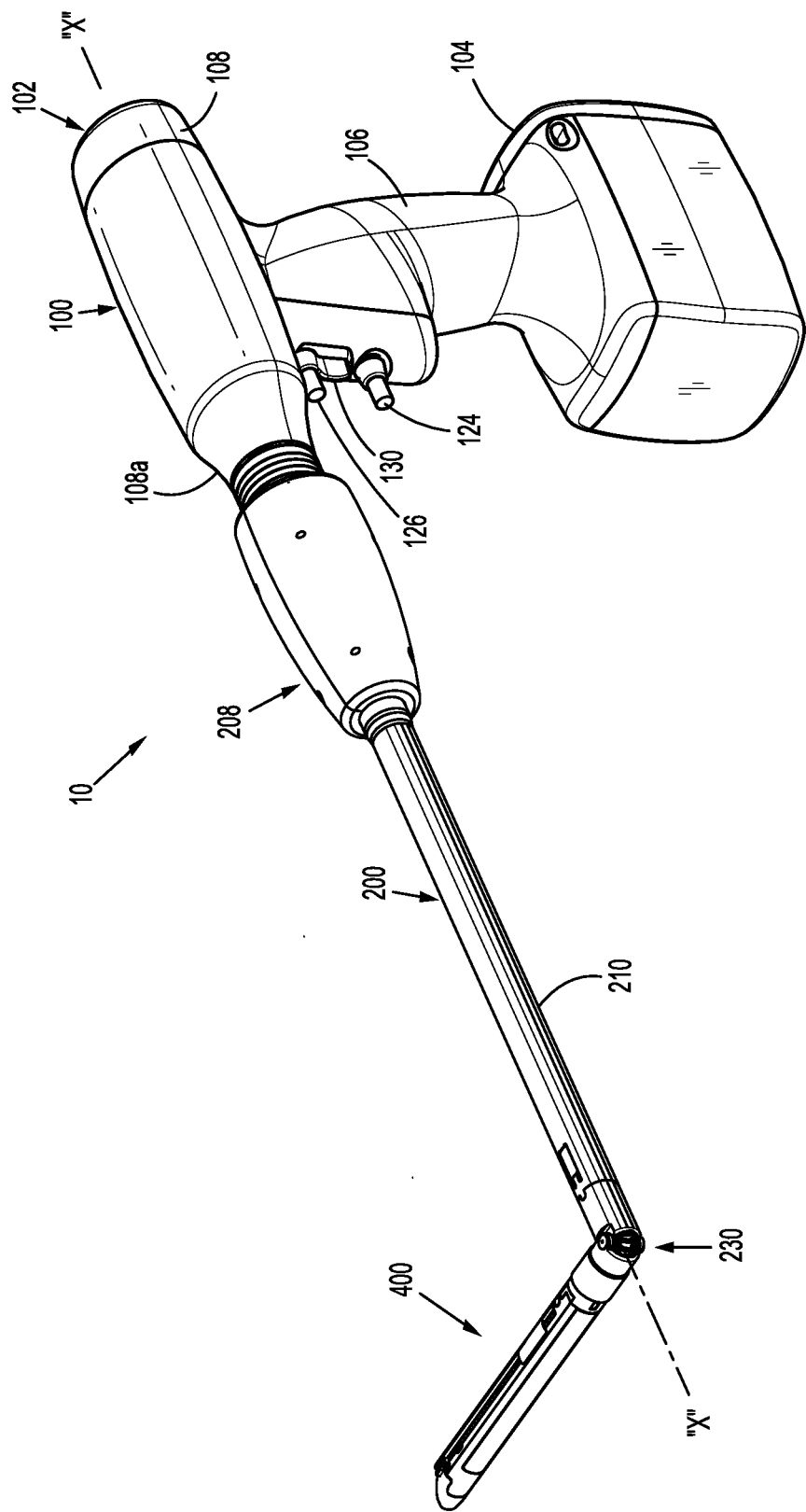
FIG. 1 is a perspective view of an electromechanical surgical system according to an embodiment of the present disclosure.

Embodiments of the presently disclosed electromechanical surgical system, apparatus and/or device are described in detail with reference to the drawings, in which like reference numerals designate identical or corresponding elements in each of the several views. As used herein the term "distal" refers to that portion of the electromechanical surgical system, apparatus and/or device, or component thereof, that are farther from the user, while the term "proximal" refers to that portion of the electromechanical surgical system, apparatus and/or device, or component thereof, that are closer to the user.

Referring initially to FIGS. 1-4, an electromechanical, hand-held, powered surgical system, in accordance with an embodiment of the present disclosure is shown and generally designated 10. Electromechanical surgical system 10 includes a surgical apparatus or device in the form of an electromechanical, hand-held, powered surgical device 100 that is configured for selective attachment thereto of a plurality of different end effectors 400, via a shaft assembly 200, that are each configured for actuation and manipulation by the electromechanical, hand-held, powered surgical device 100. In particular, surgical device 100 is configured for selective connection with shaft assembly 200, and, in turn, shaft assembly 200 is configured for selective connection with any one of a plurality of different end effectors 400.

Reference may be made to International Application No. PCT/US2008/077249, filed Sep. 22, 2008 (Inter. Pub. No. WO 2009/039506) and U.S. patent application Ser. No. 12/622,827, filed on Nov. 20, 2009, the entire content of each of which being incorporated herein by reference, for a detailed description of the construction and operation of exemplary electromechanical, hand-held, powered surgical device 100.

Generally, as illustrated in FIGS. 1-4, surgical device 100 includes a handle housing 102 having a lower housing portion 104, an intermediate housing portion 106 extending from and/or supported on lower housing portion 104, and an upper housing portion 108 extending from and/or supported on intermediate housing portion 106. Handle housing 102 defines a cavity therein in which a circuit board or controller 150 and a drive mechanism 160 are situated. Drive mechanism 160 may include a first motor 164 used to select a rotatable drive member of surgical device 100, and a second motor 166 used to drive each rotatable drive member of surgical device 100.

Circuit board 150 is configured to control the various operations of surgical device 100. In accordance with the present disclosure, handle housing 102 provides a housing in which a rechargeable battery 156, is removably situated. Battery 156 is configured to supply power to any of the electrical components of surgical device 100. While a battery 156 is shown and contemplated, any known power source may be used, such as, for example a power cord or the like.

Figure 3:
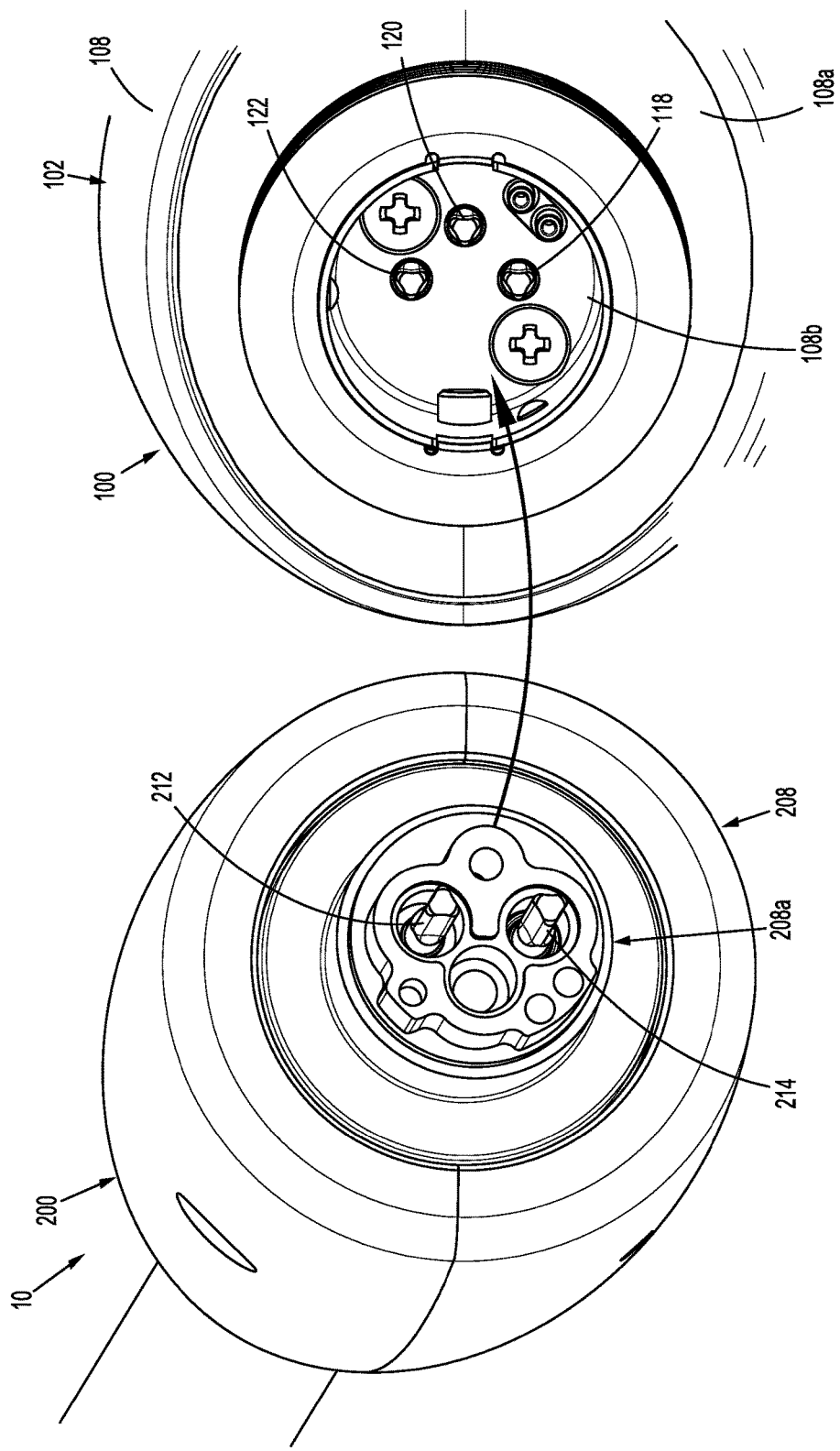
FIG. 3 is a rear, perspective view of a shaft assembly and a powered surgical device, of the electromechanical surgical system of FIGS. 1 and 2, illustrating a connection therebetween.
Figure 4:
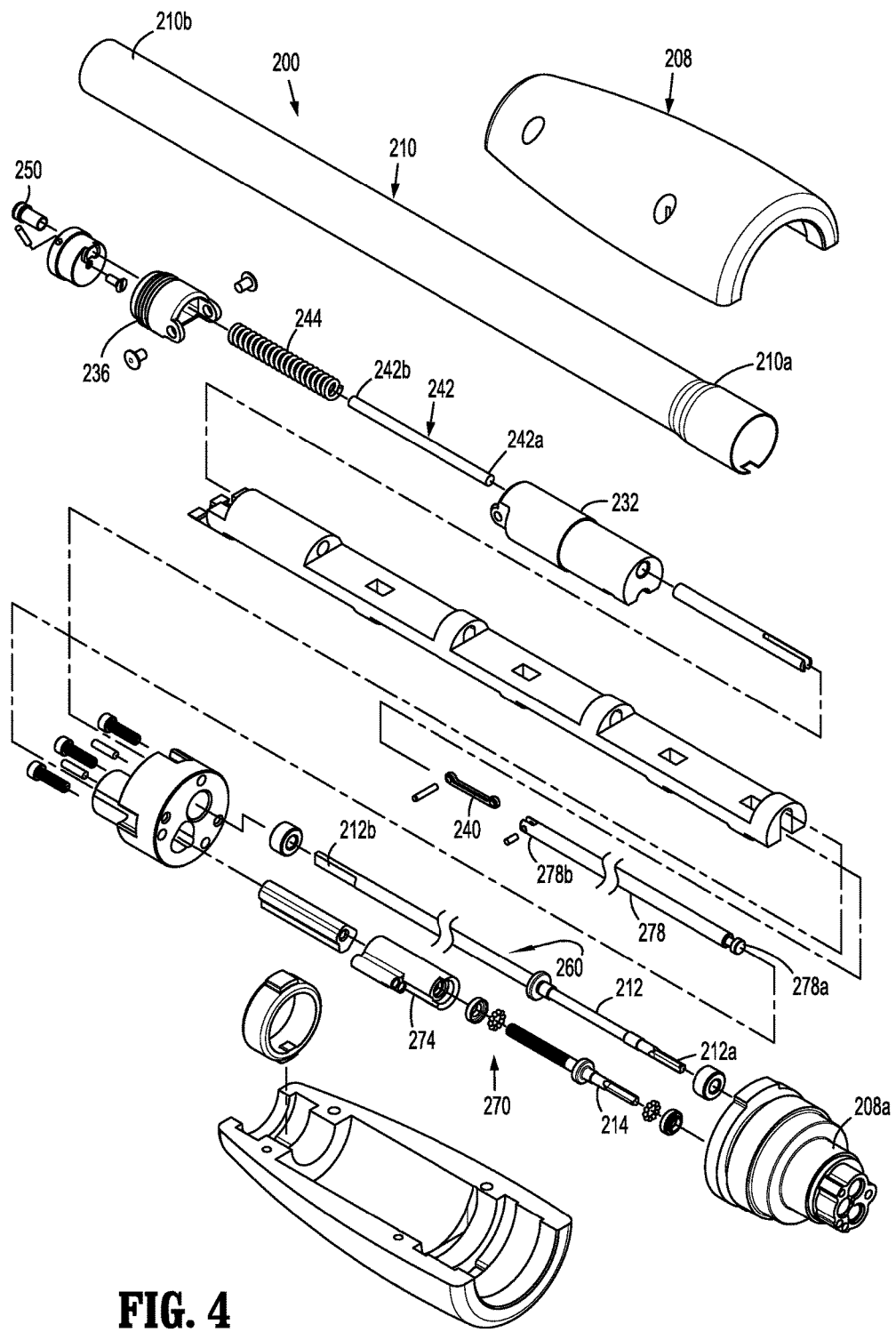
FIG. 4 is a perspective view, with parts separated, of the shaft assembly of FIGS. 1-3.
Figure 5:
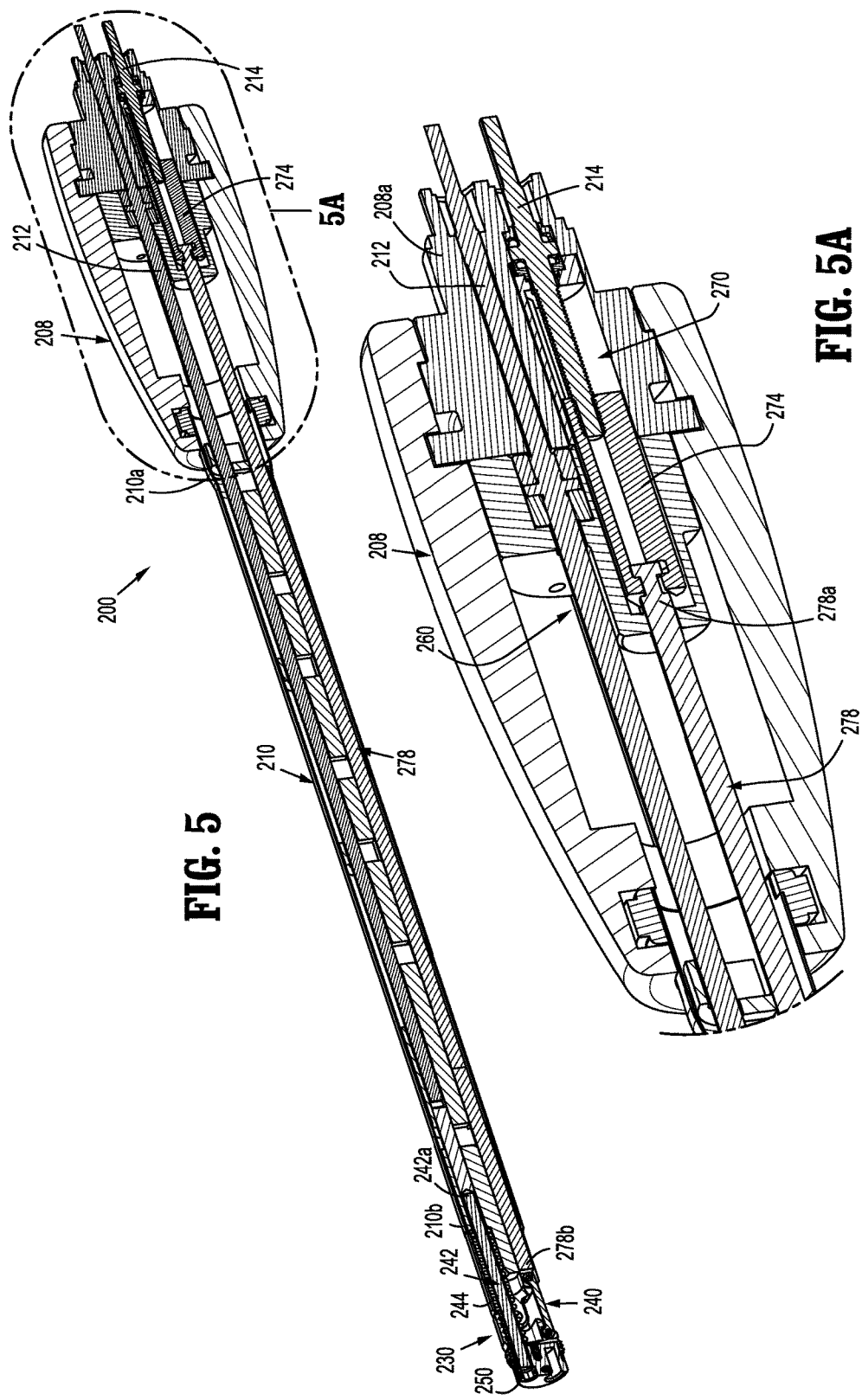
FIG. 5 is a longitudinal, cross-sectional view of the shaft assembly of FIGS. 1-3.
Figure 6:
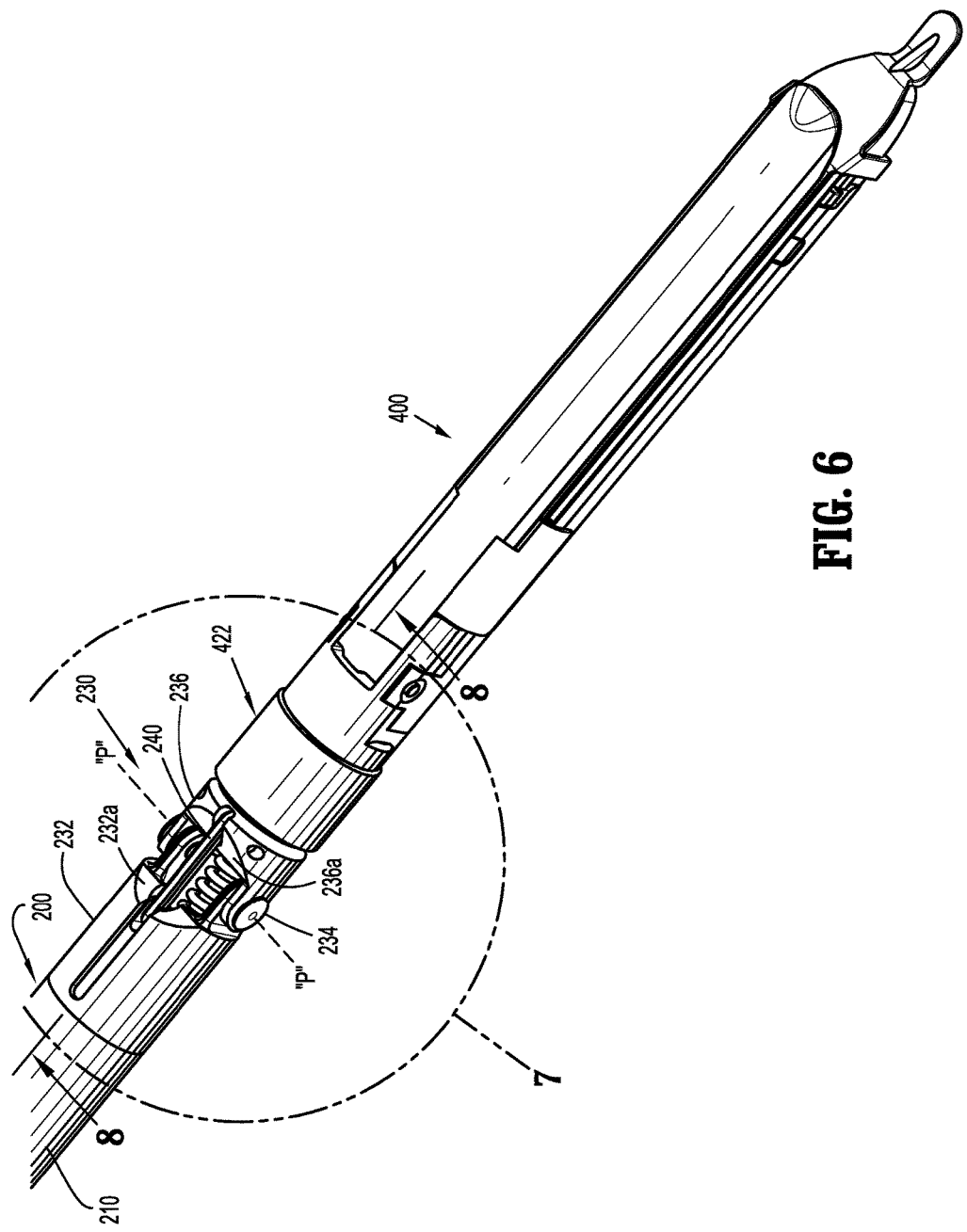
FIG. 6 is a perspective view illustrating an end effector connected to a distal end of the shaft assembly of FIGS. 1-5, oriented in a linear, non-articulated condition.
Figure 7:
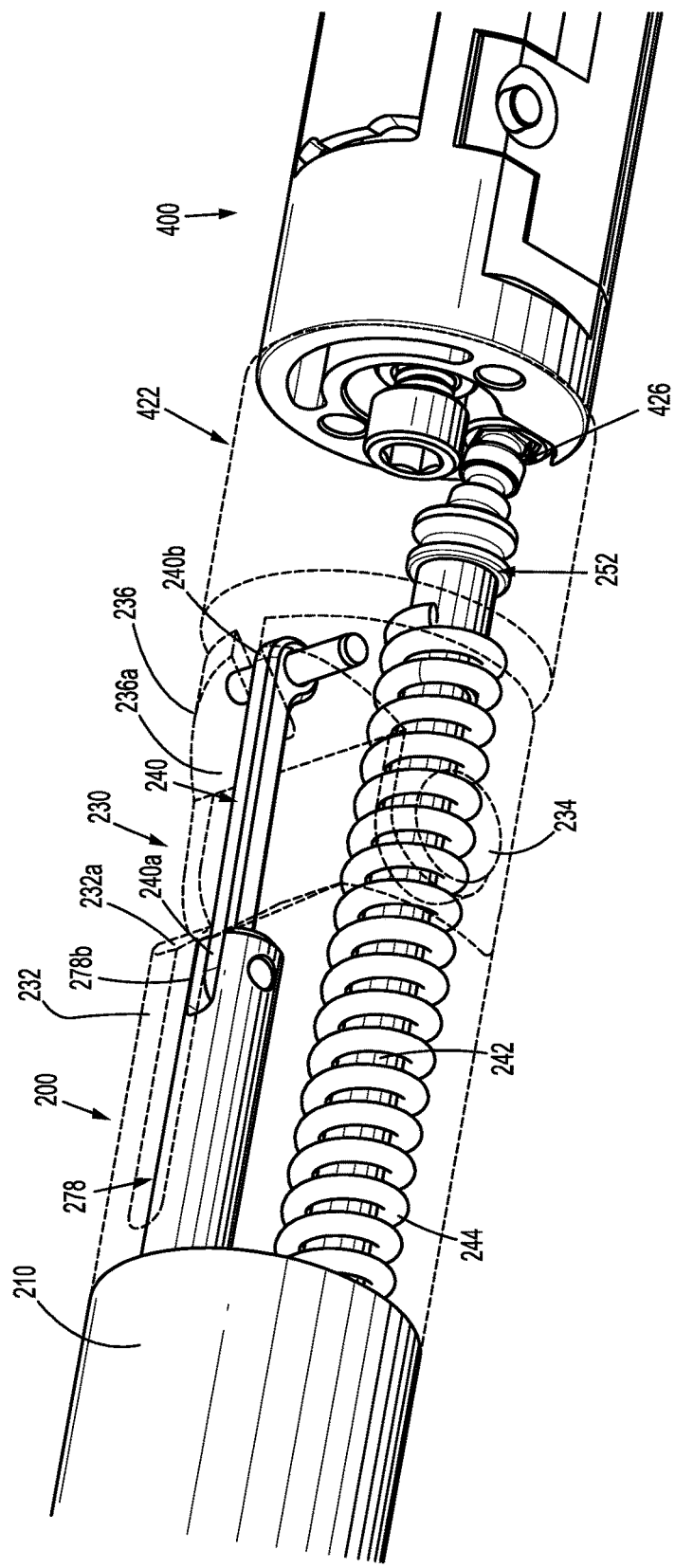
FIG. 7 is an enlarged view of the indicated area of detail of FIG. 6.

Upper housing portion 108 of handle housing 102 defines a nose or connecting portion 108a configured to accept a corresponding shaft coupling assembly 208a of transmission housing 208 of shaft assembly 200. As seen in FIG. 3, connecting portion 108a of upper housing portion 108 of surgical device 100 has a cylindrical recess 108b that receives shaft coupling assembly 208a of transmission housing 208 of shaft assembly 200 when shaft assembly 200 is mated to surgical device 100. Connecting portion 108a houses three rotatable drive connectors 118, 120, 122, each independently actuatable and rotatable by the drive mechanism (not shown) housed within handle housing 102.

Upper housing portion 108 of handle housing 102 provides a housing in which the drive mechanism (not shown) is situated. The drive mechanism is configured to drive shafts and/or gear components in order to perform the various operations of surgical device 100. In particular, the drive mechanism is configured to drive shafts and/or gear components in order to selectively move end effector 400 relative to shaft assembly 200; to rotate shaft assembly 200 and/or end effector 400, about a longitudinal axis "X" (see FIGS. 1 and 2), relative to handle housing 102; to move an upper jaw or anvil assembly 442 of end effector 400 relative to a lower jaw or cartridge assembly 432 of end effector 400, and/or to fire a stapling and cutting cartridge within cartridge assembly 432 of end effector 400.

In use, when shaft assembly 200 is mated to surgical device 100, each of rotatable drive connectors 118, 120 of surgical device 100 couples with a corresponding proximal end portion 212a, 214a of respective proximal drive shafts 212, 214 of shaft assembly 200 (see FIG. 3). In this regard, the interface between corresponding first drive connector 118 and proximal end portion 212a of first proximal drive shaft 212, and the interface between corresponding second drive connector 120 and proximal end portion 214a of second proximal drive shaft 214 are keyed such that rotation of each of drive connectors 118, 120 of surgical device 100 causes a corresponding rotation of the corresponding drive shaft 212, 214 of shaft assembly 200.

The mating of drive connectors 118, 120 of surgical device 100 with corresponding drive shafts 212, 214 of shaft assembly 200 allows rotational forces to be independently transmitted. The drive connectors 118, 120 of surgical device 100 are configured to be independently rotated by the drive mechanism. In this regard, a function selection module (not shown) of the drive mechanism selects which drive connector or connectors 118, 120 of surgical device 100 is to be driven by an input drive component (not shown) of the drive mechanism.

Since each of drive connectors 118, 120 of surgical device 100 has a keyed and/or substantially non-rotatable interface with a respective corresponding drive shaft 212, 214 of shaft assembly 200, when shaft assembly 200 is coupled to surgical device 100, rotational force(s) are selectively transferred from the drive mechanism of surgical device 100 to shaft assembly 200, and on to end effector 400, as will be discussed in greater detail below.

The selective rotation of drive connector(s) 118 and/or 120 of surgical device 100 allows surgical device 100 to selectively actuate different functions of end effector 400. As will be discussed in greater detail below, selective and independent rotation of first drive connector 118 of surgical device 100 corresponds to the selective and independent opening and closing of end effector 400, and driving of a stapling/cutting component of end effector 400. Also, the selective and independent rotation of second drive connector 120 of surgical device 100 corresponds to the selective and independent articulation of end effector 400 transverse to longitudinal axis "X" (see FIGS. 1 and 2).

In accordance with the present disclosure, the drive mechanism may include a selector gearbox assembly (not shown); a function selection module (not shown), located proximal to the selector gearbox assembly, that functions to selectively move gear elements within the selector gearbox assembly into engagement with a second motor (not shown). The drive mechanism may be configured to selectively drive one of drive connectors 118, 120 of surgical device 100, at a given time.

Figure 2:
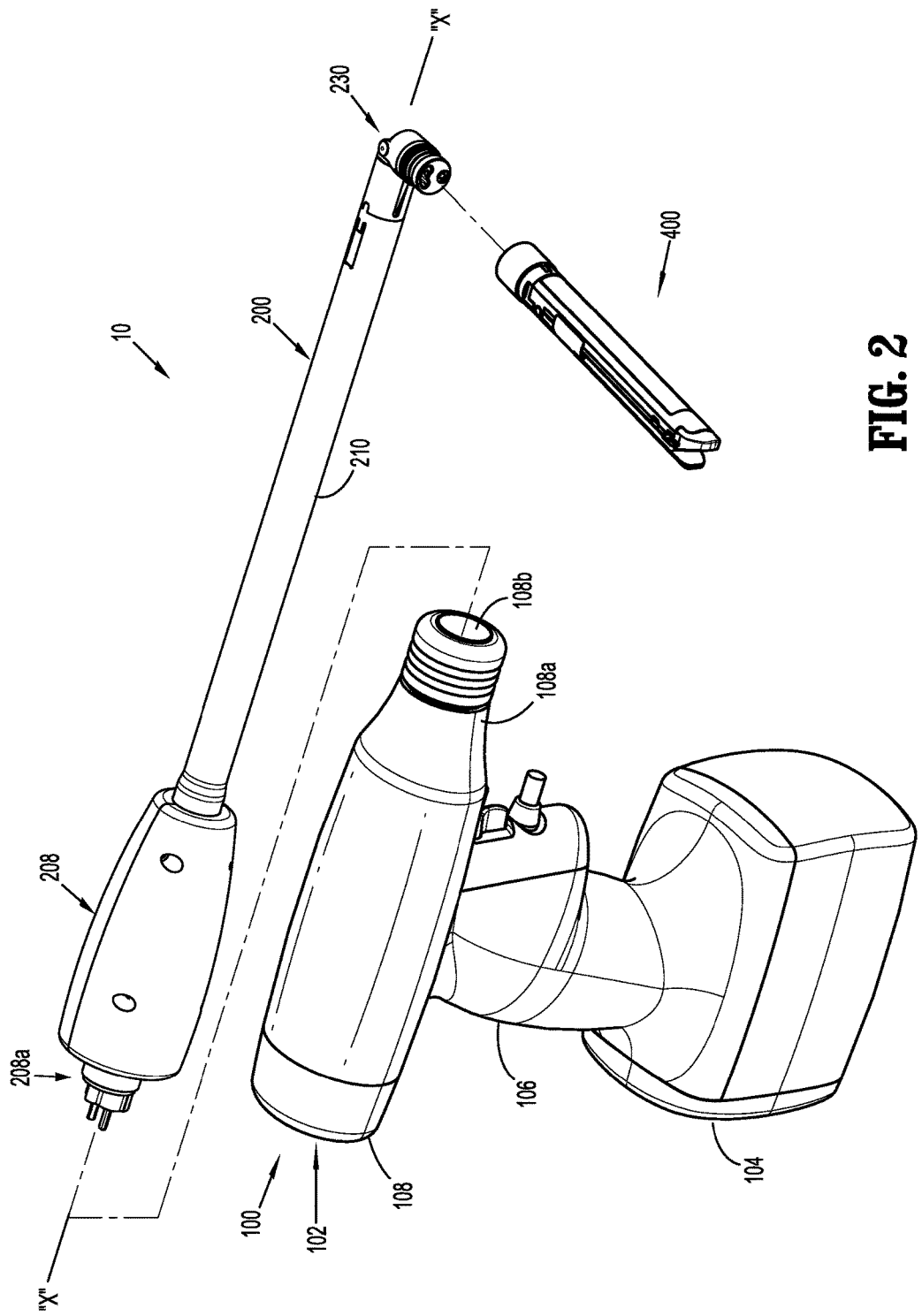
FIG. 2 is a perspective view, with parts separated, of the electromechanical surgical system of FIG. 1.
Figure 2A:
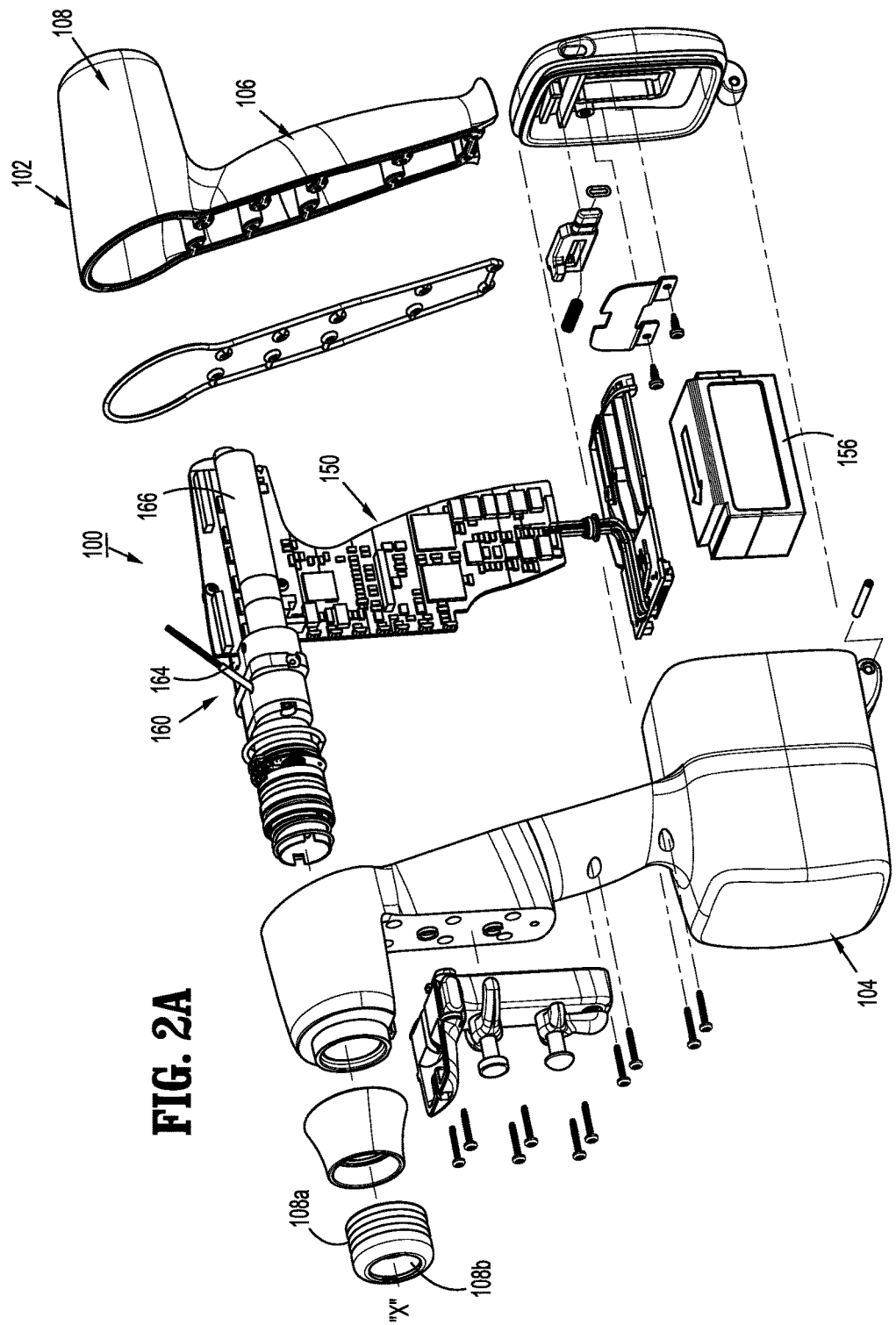
FIG. 2A is a perspective view, with parts separated, of a powered surgical device of the electromechanical surgical system of the present disclosure.

As illustrated in FIGS. 1 and 2, handle housing 102 supports a pair of finger-actuated control buttons 124, 126 and/or rocker device(s) 130 (only one rocker device being shown). Each one of the control buttons 124, 126 and rocker device(s) 130 includes a respective magnet (not shown) that is moved by the actuation of an operator. In addition, the circuit board (not shown) housed in handle housing 102 includes, for each one of the control buttons 124, 126 and rocker device(s) 130, respective Hall-effect switches (not shown) that are actuated by the movement of the magnets in the control buttons 124, 126 and rocker device(s) 130. In particular, located immediately proximal to the control button 124 is a respective Hall-effect switch (not shown) that is actuated upon the movement of a magnet within the control button 124 upon the operator actuating control button 124. The actuation of Hall-effect switch (not shown), corresponding to control button 124, causes the circuit board to provide appropriate signals to the function selection module and the input drive component of the drive mechanism to close end effector 400 and/or to fire a stapling/cutting cartridge within end effector 400.

Also, located immediately proximal to control button 126 is a respective Hall-effect switch (not shown) that is actuated upon the movement of a magnet (not shown) within control button 126 upon the operator actuating control button 126. The actuation of the Hall-effect switch, corresponding to control button 126, causes the circuit board to provide appropriate signals to the function selection module and the input drive component of the drive mechanism to open/close end effector 400.

In addition, located immediately proximal to rocker device 130 is a respective Hall-effect switch (not shown) that is actuated upon the movement of a magnet (not shown) within rocker device 130 upon the operator actuating rocker device 130. The actuation of the Hall-effect switch, corresponding to rocker device 130, causes the circuit board to provide appropriate signals to the function selection module and the input drive component of the drive mechanism to rotate end effector 400 relative to shaft assembly 200 or rotate end effector 400 and shaft assembly 200 relative to handle housing 102 of surgical device 100. Specifically, movement of rocker device 130 in a first direction causes end effector 400 and/or shaft assembly 200 to rotate relative to handle housing 102 in a first direction, while movement of rocker device 130 in an opposite, e.g., second, direction causes end effector 400 and/or shaft assembly 200 to rotate relative to handle housing 102 in an opposite, e.g., second, direction.

Turning now to FIGS. 1-14, shaft assembly 200 will be shown in detail and described. Shaft assembly 200 is configured to communicate the rotational forces of first and second rotatable drive connectors 118, 120 of surgical device 100 to end effector 400. As mentioned above, shaft assembly 200 is configured for selective connection to surgical device 100.

As seen in FIGS. 1-10, shaft assembly 200 includes an elongate, substantially rigid, tubular body 210 having a proximal end 210a and a distal end 210b; a transmission housing 208 connected to proximal end 210a of tubular body 210 and being configured for selective connection to surgical device 100; and an articulating neck assembly 230 connected to distal end 210b of elongate body portion 210.

Transmission housing 208 and tubular body 210 are configured and dimensioned to house the components of shaft assembly 200. Tubular body 210 is dimensioned for endoscopic insertion, in particular, that outer tube is passable through a typical trocar port, cannula or the like. Transmission housing 208 is dimensioned to not enter the trocar port, cannula or the like.

Transmission housing 208 of shaft assembly 200 is configured and adapted to connect to connecting portion 108a of upper housing portion 108 of surgical device 100. As seen in FIGS. 2-5A, transmission housing 208 of shaft assembly 200 includes a shaft coupling assembly 208a supported at a proximal end thereof. Shaft coupling assembly 208a is configured and adapted to connect to connecting portion 108a of upper housing portion 108 of distal half-section 110a of surgical device 100.

Transmission housing 208, and particularly shaft coupling assembly 208a, rotatably supports at least a first rotatable proximal drive shaft 212, a second rotatable proximal drive shaft 214, and optionally a third rotatable proximal drive shaft therein.

Shaft assembly 200 includes a plurality of force/rotation transmitting/converting assemblies, each disposed within transmission housing 208 and tubular body 210. Each force/rotation transmitting/converting assembly is configured and adapted to transmit/convert a speed/force of rotation (e.g., increase or decrease) of first and second drive connectors 118, 120 and optionally a third rotatable drive connector 122 of surgical device 100 before transmission of such rotational speed/force to end effector 400.

Specifically, shaft assembly 200 includes a first and a second force/rotation transmitting/converting assembly 260, 270, respectively, disposed within transmission housing 208 and tubular body 210. Each force/rotation transmitting/converting assembly 260, 270 is configured and adapted to transmit or convert a rotation of first and second drive connector 118, 120 of surgical device 100 into axial translation of a drive or articulation bar 278 of shaft assembly 200, to effectuate articulating of end effector 400; or a rotation of a drive shaft 212 of shaft assembly 200 to effectuate closing, opening and firing of end effector 400.

As seen in FIGS. 3-5A, first force/rotation transmitting/converting assembly 260 includes first rotatable proximal drive shaft 212, which, as described above, is rotatably supported within transmission housing 208. First rotatable proximal drive shaft 212 includes a proximal end portion 212a configured to support a connecting sleeve (not shown) for selective connection with first drive connector 118 of surgical device 100, and a distal end portion 212b connected to a proximal end of a flexible drive cable 242, as will be discussed in greater detail below.

In operation, as first rotatable proximal drive shaft 212 is rotated due to a rotation of first connector sleeve, as a result of the rotation of the first drive connector 118 of surgical device 100, said rotation is transmitted directly to flexible drive cable 242 of shaft assembly 200, to effectuate a closure and a firing of end effector 400, as will be discussed in greater detail below.

With continued reference to FIGS. 3-5A, second force/rotation transmitting/converting assembly 270 includes second rotatable proximal drive shaft 214, which, as described above, is rotatably supported within transmission housing 208. Second rotatable proximal drive shaft 214 includes a proximal end portion 214a configured to support a connecting sleeve (not shown) for selective connection with second drive connector 120 of surgical device 100, and a threaded distal end portion 214b.

Second force/rotation transmitting/converting assembly 270 further includes a drive coupling nut 274 rotatably coupled to threaded distal end portion 214a of second rotatable proximal drive shaft 214, and which is slidably disposed within transmission housing 208. Drive coupling nut 274 is slidably keyed within transmission housing 208 so as to be prevented from rotation as second rotatable proximal drive shaft 214 is rotated. In this manner, as second rotatable proximal drive shaft 214 is rotated, drive coupling nut 274 is translated through and/or along transmission housing 208.

Second force/rotation transmitting/converting assembly 270 further includes an articulation bar 278 having a proximal end 278a secured or connected to drive coupling nut 274. A distal end 278b of articulation bar 278 extends through tubular body 210. Articulation bar 278 is at least partially slidably supported in articulating neck assembly 230. Articulation bar 278 defines a longitudinal axis "A" off-set from the longitudinal axis "X" of shaft assembly 200.

In operation, as second rotatable proximal drive shaft 214 is rotated, due to a rotation of a second connector sleeve (not shown), as a result of the rotation of the second respective drive connector 120 of surgical device 100, threaded distal end portion 214a of second rotatable proximal drive shaft 214 is rotated. Thus, as second rotatable proximal drive shaft 214 is rotated, drive coupling nut 274 is caused to be translated axially along threaded distal portion 214a of second rotatable proximal drive shaft 214.

As drive coupling nut 274 is caused to be translated axially along second rotatable proximal drive shaft 214, articulation bar 278 is caused to be translated axially relative to tubular body 210. As will be described in greater detail below, as articulation bar 278 is axially translated, articulation bar 278 causes articulating neck assembly 230 of shaft assembly 200 to articulate and, in turn, causes end effector 400 to articulate when end effector 400 is connected to shaft assembly 200.

Turning now to FIGS. 4-14, articulating neck assembly 230 is shown and described. Articulating neck assembly 230 includes a proximal neck housing 232; and a distal neck housing 236 pivotally connected to and extending distally from proximal neck housing 232 by a pivot pin 234. Pivot pin 234 defines a pivot axis "P" (see FIG. 6) that is oriented orthogonal to the longitudinal axis "X" and extends through the longitudinal axis "X".

Articulation neck assembly 230 includes an articulation link 240 having a proximal end 240a and a distal end 240b. Proximal end 240a of articulation link 240 is pivotally connected to distal end 278b of articulation bar 278. A distal end 240b of articulation link 240 is pivotally connected to distal neck housing 236, at a location offset a transverse distance from the longitudinal axis "X".

Figure 11:
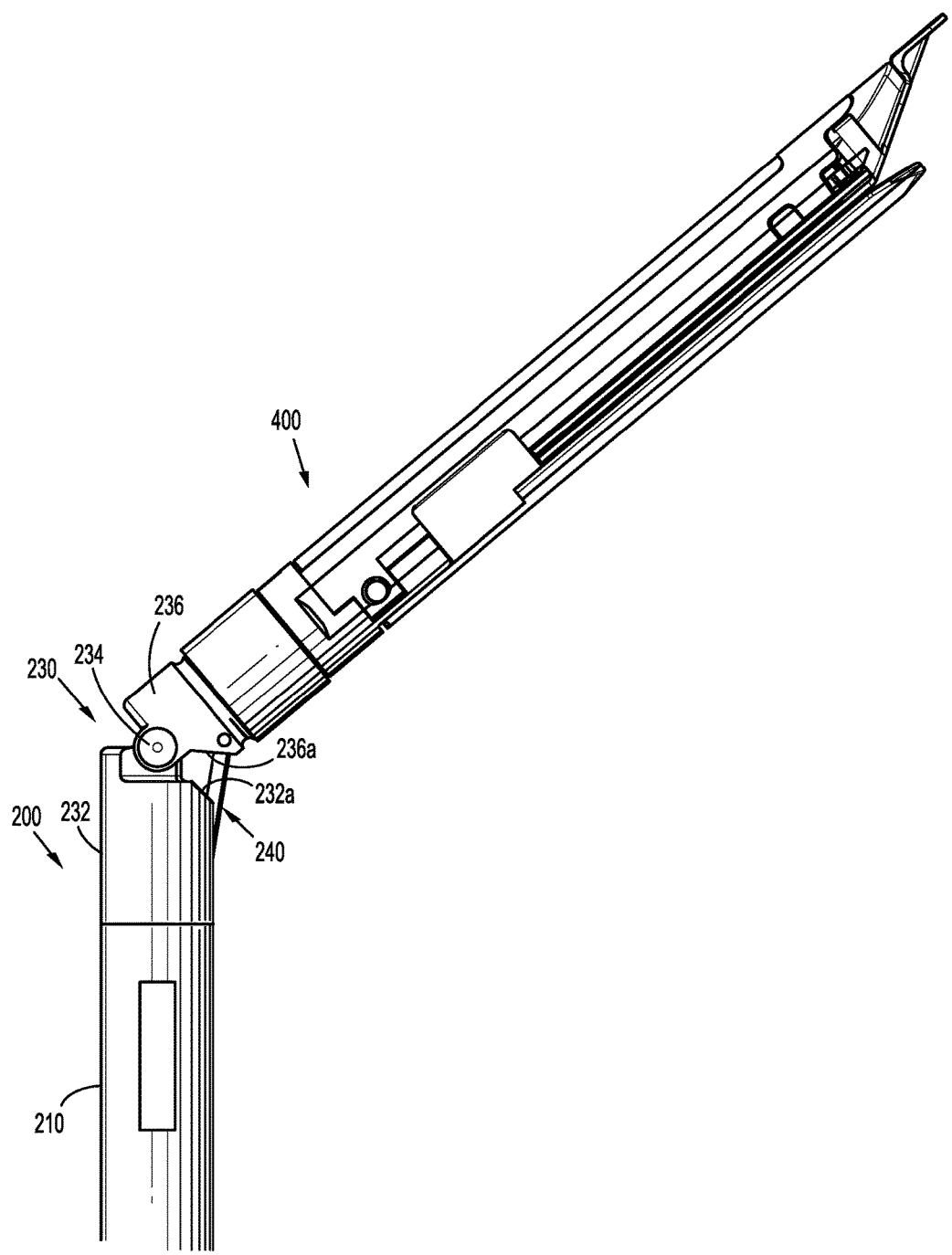
FIG. 11 is a top, plan view of the distal end of the shaft assembly and the end effector, shown in a partially articulated condition.
Figure 12:
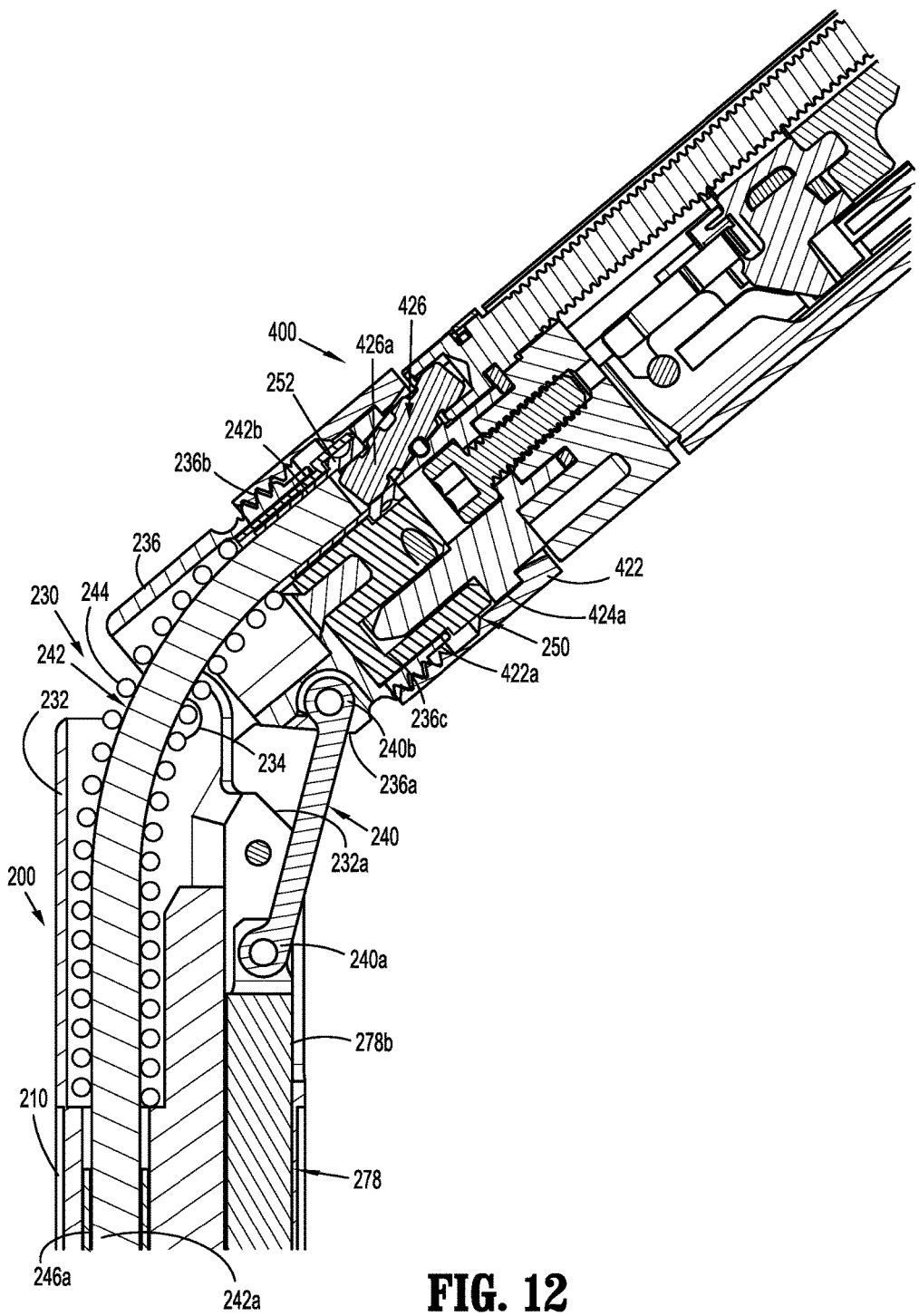
FIG. 12 is a cross-section view of the partially articulated end effector of FIG. 11.
Figure 13:
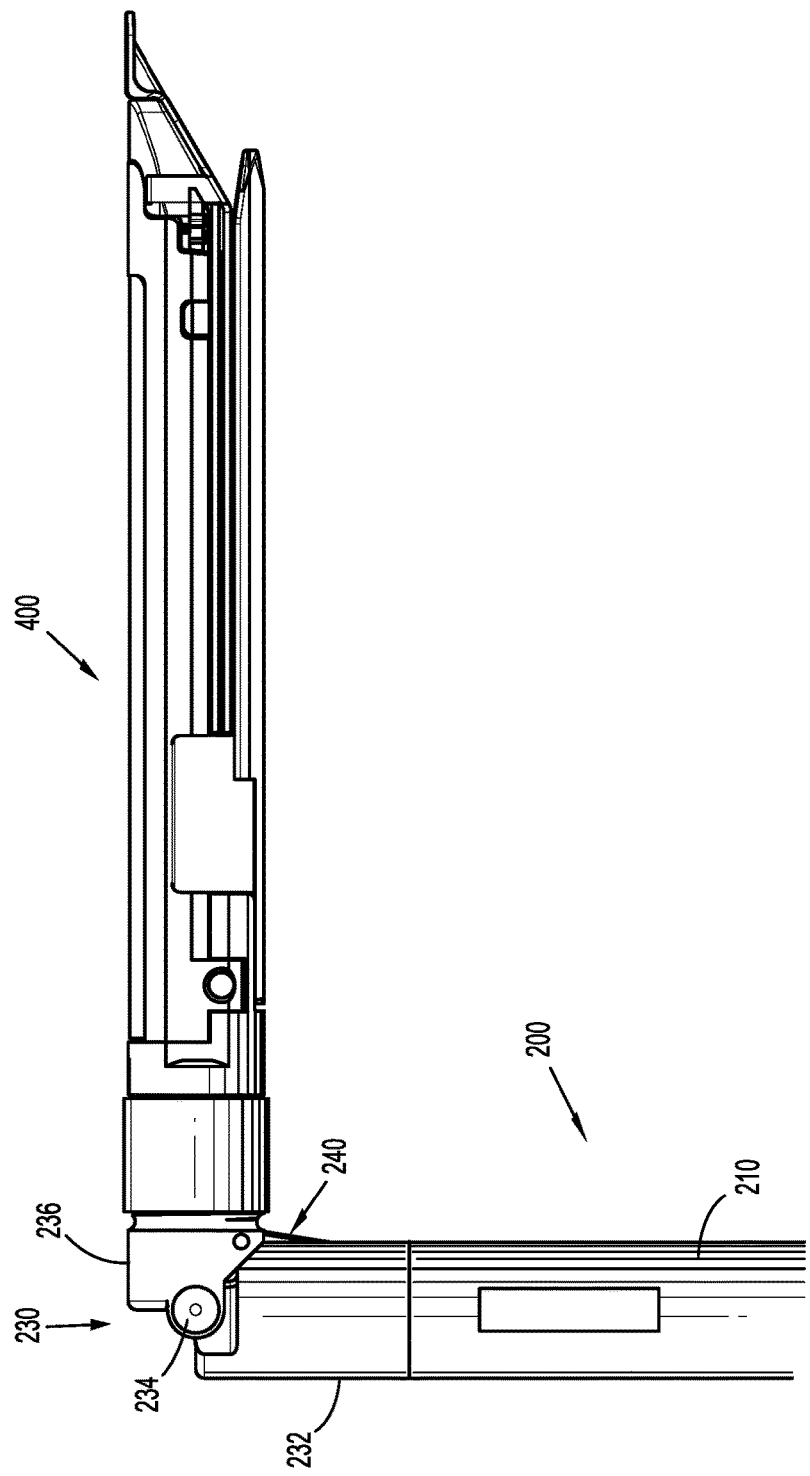
FIG. 13 is a top, plan view of the distal end of the shaft assembly and the end effector, shown in a fully articulated condition.
Figure 14:
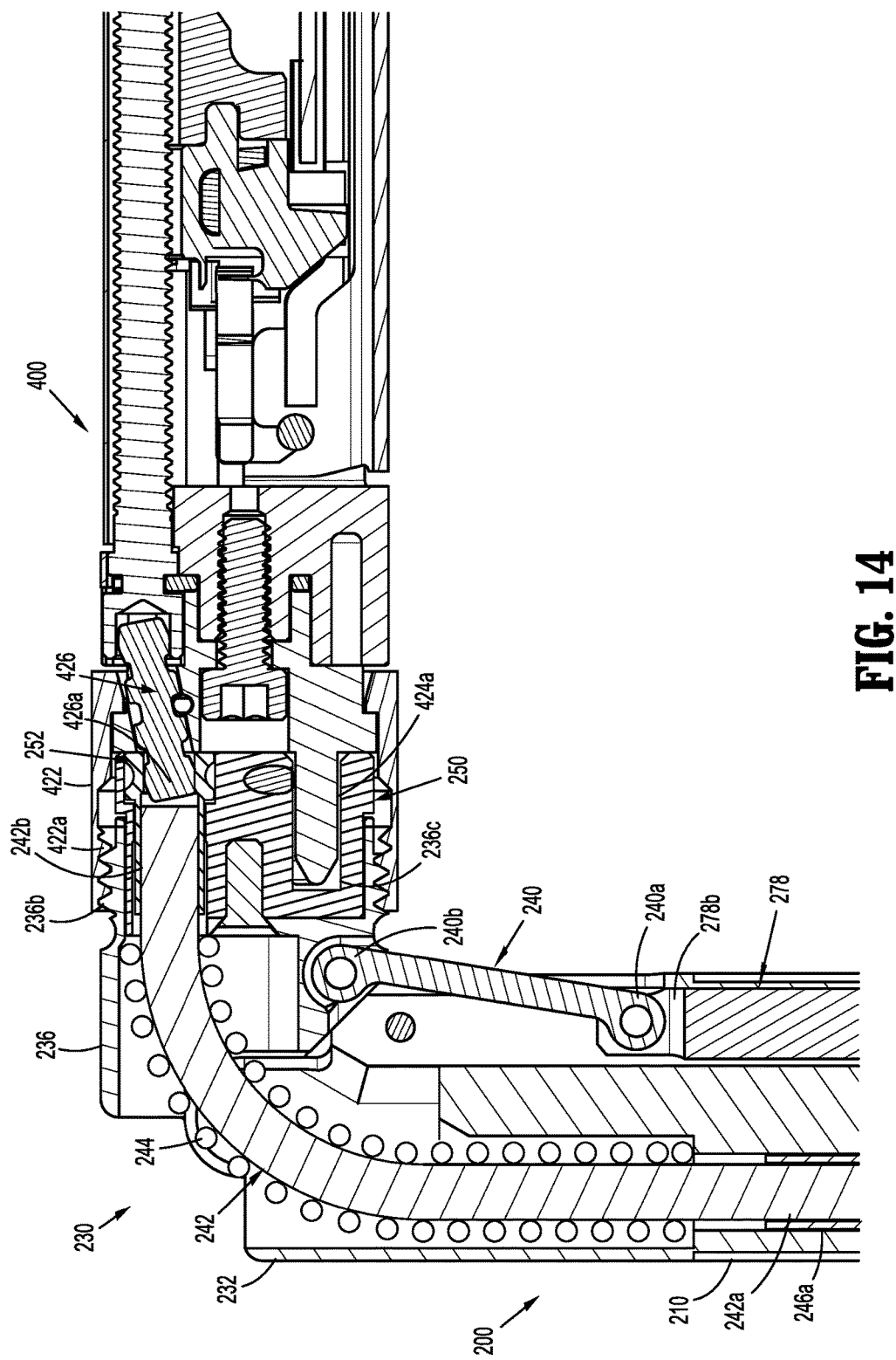
FIG. 14 is a cross-section view of the fully articulated end effector of FIG. 13.

Proximal neck housing 232 defines a chamfered distal surface 232a, and distal neck housing 236 defines a chamfered proximal surface 236a. In an embodiment, chamfered surfaces 232a, 236a are in juxtaposed relation to one another. In use, when end effector 400 is actuated to an off-axis orientation, as will be discussed in greater detail below, chamfered surfaces 232a, 236a of proximal neck housing 232 and distal neck housing 236 are approximated toward one another. Desirably, each chamfered surface 232a, 236a is angled at about 45° relative to the longitudinal axis "X". Specifically, chamfered surface 232a of proximal neck housing 232 is angled at about (−45°) relative to the longitudinal axis "X", while chamfered surface 236a of distal neck housing 236 is angled at about (+45°) relative to the longitudinal axis "X". In this manner, when end effector 400 is actuated to a maximum off-axis orientation, as seen in FIGS. 13 and 14, end effector 400 is oriented at about 90° relative to the longitudinal axis "X". In use, end effector 400 may be oriented at any angular orientation from about 0° to about 90° relative to the longitudinal axis "X", as needed or desired, such as, for example, about 45°, as seen in FIGS. 11 and 12.

In accordance with the present disclosure, distal neck housing 236 is pivotable in a single direction relative to proximal neck housing 232.

Articulating neck assembly 230 further includes a distal rotation hub 250 rotatably supported and/or coupled in a distal end of distal neck housing 236. Rotation hub 250 is rotatably supported in distal neck housing 236 such that rotation hub 250 defines an axis of rotation which is co-axial with the longitudinal axis "X". Rotation hub 250 rotatably supports a rotation nut 252. Rotation nut 252 defines a distally extending bore 252a configured and dimensioned to selectively receive a proximal head 426a of a drive axle 426 of end effector 400, as will be discussed in greater detail below.

First force/rotation transmitting/converting assembly 260 of shaft assembly 200 includes a flexible drive cable 242 rotatably supported in proximal neck housing 232 and distal neck housing 236. Flexible drive cable 242 is fabricated from a torsionally still and flexible material, such as, for example, stainless steel. Flexible drive cable 242 defines a longitudinal axis "B" off-set from the longitudinal axis "X". Flexible drive cable 242 includes a proximal end 242a that is coupled to distal end 212b of first rotatable proximal drive shaft 212. Flexible drive cable 242 includes a distal end 242b that is coupled to rotation nut 252, wherein rotation of flexible drive cable 242 results in corresponding rotation of rotation nut 252. Desirably, distal end 242b of flexible drive cable 242 is coupled to rotation nut 252 in a manner which inhibits relative rotation therebetween, and which is axially slidable relative thereto, such as, for example, being keyed thereto.

Shaft assembly 200 includes a reinforcing coil spring 244 surrounding flexible drive cable 242. In accordance with the present disclosure, reinforcing coil spring 244 is constrained at a proximal end and a distal end thereof, and is installed under compression. Reinforcing coil spring 244 functions to help keep flexible drive cable 242 from kinking during articulation of end effector 400. Reinforcing coil spring 244 also functions to help keep flexible drive cable 242 from failing due to unwinding and/or "pig tailing" during rotation thereof.

Figure 9:
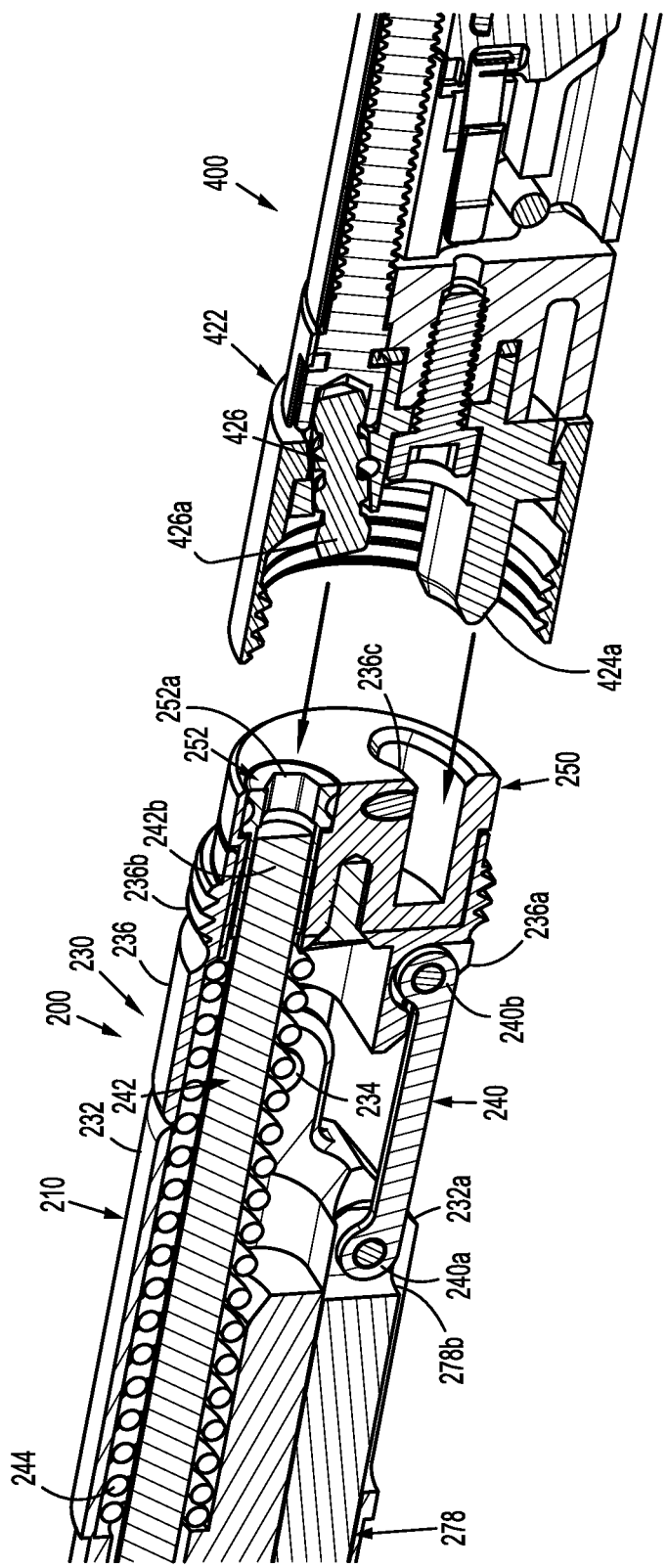
FIG. 9 is an enlarged, perspective view, with parts separated, illustrating a connection of the end effector to the distal end of the shaft assembly.
Figure 10:
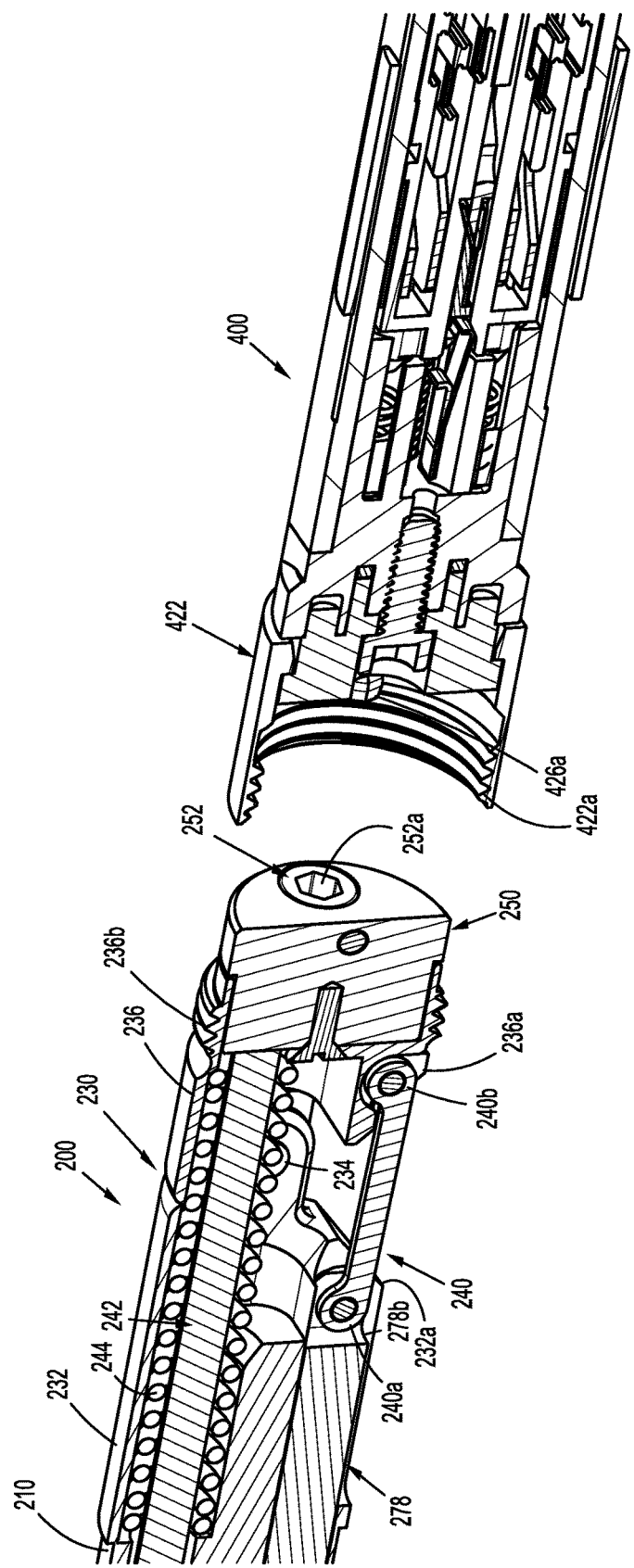
FIG. 10 is an enlarged, perspective view, with parts separated, illustrating a connection hub of the distal end of the shaft assembly connecting with the end effector.

Being that distal end 242b of flexible drive cable 242 is coupled (as described above) to rotation nut 252, and being that rotation nut 252 is rotatably supported in rotation hub 250, as rotation hub 250 is rotated about the longitudinal axis "X", distal end 242b of flexible drive cable 242 is free to rotate about the longitudinal axis "X", as illustrated in FIGS. 9 and 10.

Figure 8:
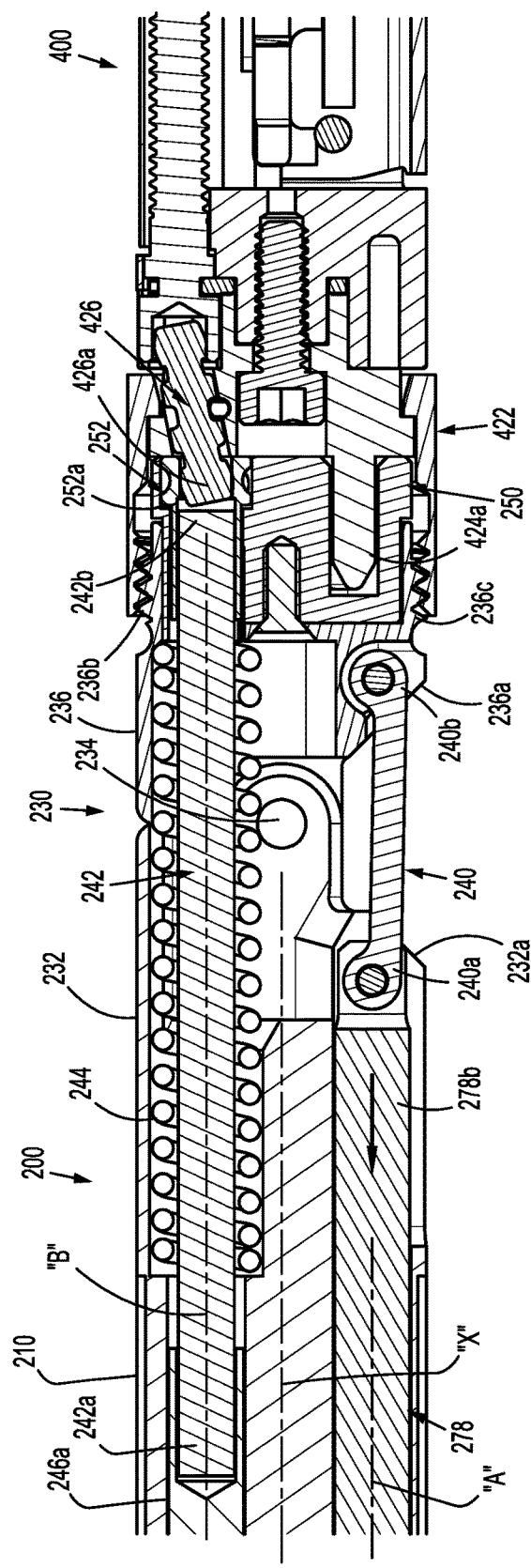
FIG. 8 is a cross-sectional view, as taken through 8-8 of FIG. 6.

As seen in FIGS. 8-10, distal neck housing 236 defines a thread 236b formed in an outer surface thereof. Thread 236b of distal neck housing 236 is configured to receive and engage a complementary thread 422a of a proximal locking nut 422 of end effector 400. In use, locking nut 422 of end effector 400 is manually coupled to distal neck housing 236 to lock and/or fix an angular orientation of end effector 400 relative to shaft assembly 200. Specifically, during use, an end user, angularly orients end effector 400 to a desired or needed angular orientation, relative to shaft assembly 200, and then tightens locking nut 422 of end effector 400 to distal neck housing 236 of shaft assembly 200 to lock and/or fix an angular orientation of end effector 400 relative to shaft assembly 200.

While a locking nut 422 is shown and described, it is contemplated that end effector 400 and shaft assembly 200 may be connected to one another via a bayonet type connection or the like.

As seen in FIGS. 8, 9, 12 and 14, distal neck housing 236 defines at least one alignment bore 236c formed in a distal surface thereof. Further, end effector 400 includes at least one corresponding alignment stem 424a projecting proximally therefrom, for receipt in alignment bore 236c formed in the distal surface of distal neck housing 236. The alignment stem 424a along with the alignment bore 236c are used to align and couple end effector 400 to distal neck housing 236 of shaft assembly 200.

In operation, as flexible drive cable 242 is rotated, due to a rotation of first rotatable proximal drive shaft 212 (as described above), said rotation is transmitted, through flexible drive cable 242, to distal end 242b of flexible drive cable 242 and on to rotation nut 252 that is rotatably supported in rotation hub 250. With end effector 400 coupled to distal neck housing 236 of shaft assembly 200, and specifically, with drive axle 426 of end effector 400 coupled to rotation nut 252, as rotation nut 252 is rotated, said rotation results in rotation of drive axle 426 of end effector 400 and actuation of end effector 400.

Also in operation, upon a rotation of second rotatable proximal drive shaft 214 (as described above), said rotation is transmitted to drive coupling nut 274 to axially translate drive coupling nut 274. As drive coupling nut 274 is translated axially, said axial translation is transmitted to articulation bar 278 to axially translate articulation bar 278. As articulation bar 278 is axially translated, for example in a proximal direction, articulation bar 278 acts on articulation link 240 to cause articulation link 240 to translate in a proximal direction. As articulation link 240 is axially translated in a proximal direction, articulation link 240 acts on distal neck housing 236 to cause distal neck housing 236 to pivot about pivot axis "P" of pivot pin 234. As distal neck housing 236 is pivoted, distal neck housing 236 acts on end effector 400 to articulate end effector 400 relative to the longitudinal axis "X".

As discussed above, end effector 400 may be manually rotated about the longitudinal axis "X". Being that drive cable 242 is flexible, as end effector 400 is rotated about the longitudinal axis "X", causing distal neck housing 236 to also be rotated about the longitudinal axis "X", distal end 242b of flexible drive cable 242 is also rotated about the longitudinal axis "X". In accordance with the present disclosure, distal neck housing 236, and in turn distal end 242b of flexible drive cable 242 is capable of rotating about +/−90° about the longitudinal axis "X".

Reference may be made to U.S. patent application Ser. No. 13/280,898, filed on Oct. 25, 2011, entitled "Apparatus for Endoscopic Procedures", for a detailed discussion of the construction and operation of end effector 400. End effector 400 may be configured and adapted to apply a plurality of linear rows of fasteners, which in embodiments may be of various sizes, and which, in certain embodiments may have various lengths or rows, e.g., about 30, 45 and 60 mm in length.

It will be understood that various modifications may be made to the embodiments disclosed herein. For example, surgical device 100 and/or cartridge assembly 432 need not apply staples but rather may apply two part fasteners as is known in the art. Further, the length of the linear row of staples or fasteners may be modified to meet the requirements of a particular surgical procedure. Thus, the length of the linear row of staples and/or fasteners within a staple cartridge assembly may be varied accordingly. Therefore, the above description should not be construed as limiting, but merely as exemplifications of preferred embodiments. Those skilled in the art will envision other modifications within the scope and spirit of the claims appended thereto.

What is claimed is:

1. A shaft assembly for interconnecting at least one rotatable drive shaft of a hand-held electromechanical surgical device and an end effector, the shaft assembly comprising:
   a shaft coupling assembly including a drive member configured to connect to a rotatable drive shaft of a surgical device;
   an outer tube having a proximal end portion supported by the shaft coupling assembly, the outer tube defining a central longitudinal axis;
   a neck portion including:
     a proximal neck portion supported at a distal end portion of the outer tube;
     a distal neck portion pivotally connected to the proximal neck portion, the distal neck portion configured to connect to an end effector;
   a hub rotatably supported at the distal neck portion, the hub rotatable about an axis of rotation coaxial with the central longitudinal axis; and
   a rotation nut rotatably supported in the hub and connected to a distal end portion of the drive member, the rotation nut radially offset from the central longitudinal axis and configured to selectively connect to a rotatable drive axle of an end effector.

2. The shaft assembly according to claim 1, further comprising:
   an articulation rod at least partially slidably supported in the proximal neck portion; and
   an articulation link having a proximal end portion pivotally connected to the articulation rod and a distal end portion pivotally connected to the distal neck portion, wherein axial movement of the articulation link pivots the distal neck portion relative to the proximal neck portion.

3. The shaft assembly according to claim 1, wherein the proximal neck portion is pivotable about a pivot axis that is transverse relative to the central longitudinal axis.

4. The shaft assembly according to claim 1, wherein the distal neck portion is pivotable only in a single direction relative to the proximal neck portion.

5. The shaft assembly according to claim 1, wherein the distal neck portion defines a proximal chamfered surface and the proximal neck portion defines a distal chamfered surface, the proximal chamfered surface and the distal chamfered surface define a maximum pivot angle of the distal neck portion relative to the proximal neck portion.

6. The shaft assembly according to claim 1, wherein the drive member is a flexible drive cable configured to operatively connect at its proximal end portion to a drive shaft of a hand-held surgical device and is offset radially from the central longitudinal axis of the outer tube.

7. The shaft assembly according to claim 6, wherein the flexible drive cable is sheathed in a coil spring.

8. An electromechanical surgical system, comprising:
   a hand-held surgical device including a device housing defining a connecting portion and at least one rotatable drive shaft;
   an end effector configured to perform at least one function, the end effector including a rotatable drive axle; and
   a shaft assembly for selectively interconnecting the end effector and the surgical device, the shaft assembly including:
     a shaft coupling assembly configured to connect to the connecting portion, the shaft assembly including a drive member configured to connect to the rotatable drive shaft;
     an outer tube having a proximal end portion supported by the shaft coupling assembly, the outer tube defining a central longitudinal axis;
     a neck portion including:
       a proximal neck portion supported at a distal end portion of the outer tube;
       a distal neck portion pivotally connected to the proximal neck portion, the distal neck portion configured to connect to the end effector;
     a hub rotatably supported at the distal neck portion, the hub rotatable about an axis of rotation coaxial with the central longitudinal axis; and
     a rotation nut rotatably supported in the hub and connected to a distal end portion of the drive member, the rotation nut radially offset from the central longitudinal axis and configured to selectively connect to the rotatable drive axle.

9. The electromechanical surgical system according to claim 8, further comprising:
   an articulation rod at least partially slidably supported in the proximal neck portion; and
   an articulation link having a proximal end portion pivotally connected to the articulation rod and a distal end portion pivotally connected to the distal neck portion, wherein axial movement of the articulation link pivots the distal neck portion relative to the proximal neck portion.

10. The electromechanical surgical system according to claim 8, wherein the proximal neck portion is pivotable about a pivot axis that is transverse relative to the central longitudinal axis.

11. The electromechanical surgical system according to claim 8, wherein the distal neck portion is pivotable only in a single direction relative to the proximal neck portion.

12. The electromechanical surgical system according to claim 8, wherein the distal neck portion defines a proximal chamfered surface and the proximal neck portion defines a distal chamfered surface, the proximal chamfered surface and distal chamfered surface define a maximum pivot angle of the distal neck portion relative to the proximal neck portion.

13. The electromechanical surgical system according to claim 8, wherein the drive member is a flexible drive cable configured to operatively connect at its proximal end portion to a drive shaft of a hand-held surgical device and is offset radially from the central longitudinal axis of the outer tube.

14. The electromechanical surgical system according to claim 13, wherein the flexible drive cable is sheathed in a coil spring.

15. The electromechanical surgical system according to claim 8, wherein the end effector includes a pair of opposing jaw members configured to grasp tissue.

16. The electromechanical surgical system according to claim 15, wherein the rotatable drive axle is configured to move at least one of the opposing jaw members relative to the other opposing jaw member.

17. The electromechanical surgical system according to claim 16, wherein one of the opposing jaw member includes at least one fastener.

18. The electromechanical surgical system according to claim 17, wherein the rotatable drive axle is configured to eject the at least one fastener from one of the opposing jaw members.

* * * * *